(12) United States Patent
Ueyama et al.

(10) Patent No.: US 6,245,906 B1
(45) Date of Patent: Jun. 12, 2001

(54) **PROBES FOR THE DIAGNOSIS OF INFECTIONS CAUSED BY *STREPTOCOCCUS PYOGENES***

(75) Inventors: Hiroshi Ueyama, Osakak; Kanako Abe, Yawata; Hiroyuki Keshi; Akio Matsuhisa, both of Osaka, all of (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/381,862

(22) PCT Filed: Mar. 23, 1998

(86) PCT No.: PCT/JP98/01288
§ 371 Date: Jan. 11, 2000
§ 102(e) Date: Jan. 11, 2000

(87) PCT Pub. No.: WO98/42845
PCT Pub. Date: Oct. 1, 1998

(30) Foreign Application Priority Data

Mar. 25, 1997 (JP) .................................................... 9-071077

(51) Int. Cl.[7] .............................. C07H 21/04; C12Q 1/68
(52) U.S. Cl. .......................... 536/24.32; 435/6; 536/24.3; 536/23.1

(58) Field of Search .................................. 536/23.1, 24.3, 536/24.32; 435/6

(56) References Cited

U.S. PATENT DOCUMENTS 5,552,273 * 9/1996 Cleuziat ................................... 435/6

OTHER PUBLICATIONS

Podbielski, A. et al., "Molecular characterization of group A streptococcal (GAS) oilgopeptide permease (Opp) and its effect on cysteine protease production," *Mol. Microbiol.*, 21(5):1087–1099 (Sep., 1996).
PCT International Preliminary Examination Report, International Application No. PCT/JP/98/01288 filed Mar. 23, 1998, dated Mar. 23, 1998.

* cited by examiner

*Primary Examiner*—W. Gary Jones
*Assistant Examiner*—Jeanine Goldberg
(74) *Attorney, Agent, or Firm*—Marshall, O'Toole, Gerstein, Murray & Borun

(57) ABSTRACT

The DNA from the bacteria *Streptococcus pyogenes* is extracted, then completely digested with restriction enzyme HindIII, followed by cloning into a suitable vector to select a probe comprising DNA which is essentially contained in *Streptococcus pyogenes*, then the sequence of the probe is elucidated.

20 Claims, 1 Drawing Sheet

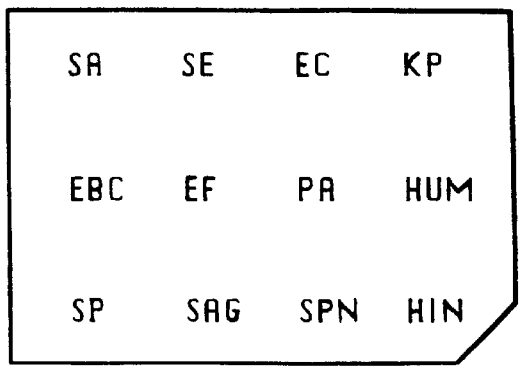
SA:*S.aureus* /SE:*S.epidermidis* /EC:*E.coli* /KP:*K.pneumoniae* / EBC:*E.cloacae* /EF:*E.faecalis* /PA:*P.aeruginosa* /HUM:U937 genomic DNA /SP:*S.pyogenes* /SAG:*S.agalactiae* /SPN: *S.pneumoniae* /HIN:*H.influenzae*
FIG. IA
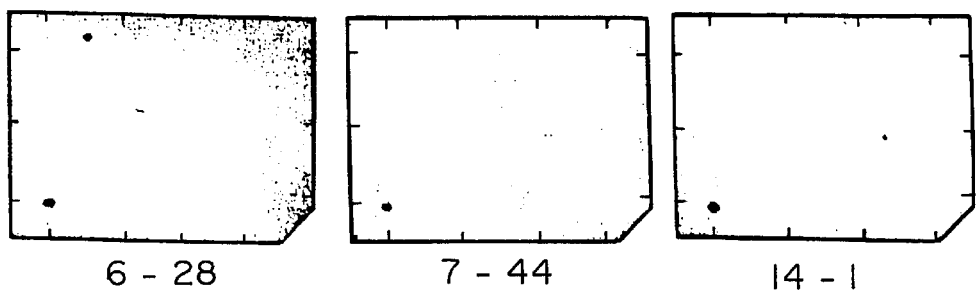
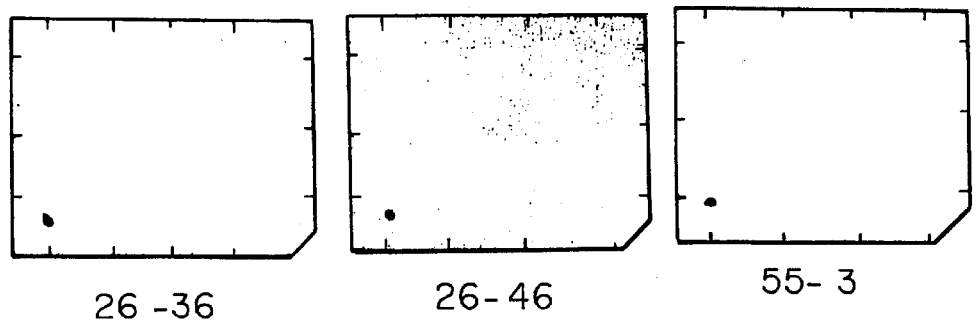
FIG. IB

PROBES FOR THE DIAGNOSIS OF INFECTIONS CAUSED BY *STREPTOCOCCUS PYOGENES*

FIELD OF THE INVENTION

The present invention relates to a probe which is useful for detecting and identifying *Streptococcus pyogenes*, the causative bacteria of infectious diseases such as pharyngitis, rheumatic fever, nephritis, erysipelas, scarlatina, sepsis and the like.

BACK GROUND ART

Generally, the diseases caused by infection of pathogenic microorganisms are called infectious diseases. In pathology, "infection" is defined as an invasion of pathogenic microorganisms (hereinafter referred to as "bacteria") and an establishment of footholds for the growth in the host organism by the pathogenic microorganisms. Thereafter, the outbreak of the disease states caused by proliferation of the pathogenic microorganisms in vivo depends upon the relationship between the resistance of the host and the virulence of the bacteria.

Streptococcus is a genus of gram-positive facultative or obligate anaerobe, which exhibits the chain like arrangement. According to the characteristic appearances of hemolytic rings formed around the colonies grown on blood agar medium, the member of this genus is classified into three types: α, β, and γ. Moreover, the members of this genus are further classified into 20 groups from A to V (except I and J) in dependence upon their antigenicity of C-polysaccharide contained in the bacteria (Lancefield classification).

*Streptococcus pyogenes* is a member of Streptococcus Group A under Lancefield classification, which shows β-type hemolysis (i.e., complete hemolysis), and is of clinical importance as causative bacteria of human pharyngitis, tonsillitis, scarlatina, erysipelas, puerperal fever, sepsis and the like. It is also known as the causative bacteria for the allergic diseases which are referred to as post-streptococcal diseases such as rheumatic fever or nephritis secondary to the initial infection. Furthermore, in recent years, the cases that exhibit severe septic shock with myositis (fulminant type Streptococcus Group A infection) due to *Streptococcus pyogenes* infection have been also reported.

The patient suffering from pharyngitis upon *Streptococcus pyogenes* infection generally complains sore throat with significant erythrogenic pharynx and trachelopanus as well as pharyngeal pain, therefore, these clinical symptoms may suggest the infection of the bacteria and lead to the possible diagnosis. However, it is desirable to avoid the unnecessary administration of antibacterial agents while the optimal chemical therapy is extremely important to prevent the complications secondary to the infection, and in view of some cases not accompanied by evident clinical symptoms, development of the rapid and accurate bacteriological diagnosis has been desired.

In addition, in the case of fulminant type Streptococcus Group A infection, more than 50% of the cases were reported to result in complications with severe necrotizing tasciitis, therefore it can be easily progressed to multiple organ failure and even to death.

*Streptococcus pyogenes* is generally known to be highly sensitive to β-lactam agents such as ampicillin and cefaclor. However, approximately 30% of the bacterial strains are highly resistant to erythromycin, and the appearance of ofloxacin resistant strains has also been reported, therefore, the most attention has to be paid at administration with macrolide derivatives or new-quinolone derivatives.

Consequently, it is essentially important to perform the accurate diagnosis at an early stage of infection and select the optimal antibacterial agents in the cases of the infectious diseases caused by *Streptococcus pyogenes* as described above.

In general biological procedure, it is mandatory to: (1) analyze the clinical symptoms; (2) culture the specimen; and (3) isolate and identify *Streptococcus pyogenes* from the cultures, and then the therapeutic strategy is determined after these items are sufficiently examined.

The method to identify *Streptococcus pyogenes* comprises direct smear culturing of the specimen on a blood agar plate which is supplemented with 5% sheep or horse defibrinated blood and monitoring the characteristic appearances of the hemolytic rings around the colonies grown on the plate.

However, it is always accompanied by the difficulties in the identification of the causative bacteria. Actual identification of the causative bacteria is quite difficult because of a variety of shapes of the colonies which are formed dependent upon the culture conditions, thus, the identification is avoided. Also, the bacteria from the specimen have to be proliferated for a long time in the appropriate medium to the number large enough for applying the drug sensitivity test, and then at least 3 to 4 days of incubation period is required to attain the result of the test. Thus the rapid diagnosis can not be achieved in accordance with the above process. Additionally, in cases of the diagnosis of the patients who had already been treated with a large dose of antibiotics when the possible infection was suspected, the growth and proliferation of the bacteria may be prevented even if the bacteria are present in the specimen. Accordingly, the feasibility of successful culture of the bacteria from these specimen may become extremely low.

Furthermore, alternative subroutine methods developed heretofore may include: an instrumental analysis method of constituents of bacteria and metabolic products from bacteria (See Yoshimi Benno, "Quick identification of bacteria with gas chromatography", Rinsho Kensa, Vol. 29, No.12 pp.1618–1623, November 1985, Igaku Shoin.); a method utilizing a specific antibody (See Japanese Patent Provisional Publication No.60-224068.); and a hybridization method utilizing a specificity of DNA (Japanese Patent Provisional Publication No. 61-502376), however, any of which requires the steps for isolation of the bacteria, as well as the steps for culturing and growing the bacteria.

On the other hand, an established method based on the function of the phagocyte in the infectious diseases has been proposed, wherein a stained smear of buffy coat in which leukocytes constituents in the blood sample are concentrated is examined under an optical microscope. Generally speaking, the detection rate of bacteria in buffy coat specimens from adult bacteremia patients is 30% at most, which is similar to that in blood specimens from ear lobes, however, it was reported that in case that the patients are newborn children, the bacteria could be detected in seven cases in ten (70%). Therefore, information concerning the presence of bacteria in peripheral blood obtained by a microscopic prospection on a smear can provide an important guiding principle for the therapeutic treatment.

The above mentioned conventional methods necessitate the pretreatment which requires at least three to four days in total, containing one to two days for the selective isolation of bacteria from a specimen, one day for proliferating cultivation, and one or more days for operation of fixation, and the culture thereof should be continued in practice until the bacteria grow enough, therefore, the pretreatment may require one week or more days. In addition, any bacteria other than the causative bacteria may be contaminated during the culture step in some cases, and such contaminants may not be distinguished from the causative bacteria.

More importantly, as mentioned above, because many of the causative bacteria in the specimen to be proliferated and detected have been uptaked into phagocytes, and are already dead or in a bacteriostatic state due to the antibiotics administered, the number of bacteria that can be grown may be small even under appropriate conditions for the culture of the causative bacteria, thereby, the actual detection rate of bacteria is as low as about 10% when the clinical culture specimen is employed. In the other words, for the present, 90% of the examined blood from the patient clinically suspected as suffering from the infection of Streptococcus pyogenes could not be identified for the presence of the bacteria after all, even though the culture is continued for further one or more days.

Although the determination of the causative bacteria and selection of the antibiotics suitable for killing the bacteria as quick as possible have been eminently desired, in light of the present situation as above, the presently employed practice depends upon a therapeutic treatment which is initiated when the infection of Streptococcus pyogenes is clinically suspected without awaiting the results of the detection of the causative bacteria. That; is to say, a trial and error method has been practiced wherein an antibiotic having the effectiveness for the widest range of spectra against many kinds of bacteria is administered first, and next, if the antibiotic is shown to be not effective after one or two days, another antibiotic will be tested.

Recently, rapid methods for the diagnosis of the infections of Streptococcus pyogenes to immunologically detect the bacteria using the procedures such as latex agglutination assay, co-agglutination assay, enzyme immunoassay, gold particle assay and liposome immunoassay have been developed. All of these methods are carried out by extracting C-polysaccharide on the surfaces of the bacterial bodies of Streptococcus pyogenes with nitrous acid or enzymes, and detecting the presence of the bacteria using the polysaccharide as an antigen.

However, the above immunological methods are problematic because the results thereof are often inconsistent with the results obtained by the culture method (namely, indicating false positive or false negative results), and because the manipulation for carrying out the methods are complicated.

Further, species specificity of this immunological method is not satisfactory due to the properties of this diagnosis method in which antigen-antibody reactions are utilized, namely, detection of the bacteria except for Streptococcus pyogenes, which carry Group A antigen (e.g., Streptococcus anginosus, and the like) may be obliged.

Meanwhile, a diagnostic guideline for the clinical diagnosis of the infections caused by fulminant Group A Streptococcus has been also proposed JAMA, Vol.269, 390–391, 1993), however, it is not applicable to the early diagnosis.

Although the infectious diseases caused by Streptococcus pyogenes are diseases of which rapid and accurate diagnosis has been required, the conventional diagnosis method could not have complied with such demands.

DISCLOSURE OF THE INVENTION

The present invention was accomplished in view of the above-described problems in this art, and is directed to probes which have the specific reactivities toward DNA or RNA derived from causative bacteria of infectious diseases, specifically Streptococcus pyogenes, and to elucidation of the nucleotide sequences of the portions of the gene essentially derived from Streptococcus pyogenes, which should be comprised in the probe.

Accordingly, the bacterial DNA still included in the bacteria but in the process of breakdown through phagocytosis by phagocytes can be significantly detected based on its specificity using hybridization method. Therefore, rapid and accurate detection of the causative bacteria of infectious diseases can be achieved without culturing and proliferation of the bacteria. Moreover, identification of the causative bacteria can be accomplished through DNA amplification using PCR method without the hybridization process when a primer is designed with reference to the nucleotide sequence information of the probes of the present invention.

In addition, the probe used for the hybridization may be labeled with non-radioactive agent. If biotinylated probe is used for example, the detection can be carried out in a general examination laboratory not having a facility for radioisotope handling. Thus, operation for the detection can be practiced in a rapid and simple way.

BRIEF DESCRIPTION OF DRAWINGS

FIG. 1(a) is a drawing which shows the positions of the originated bacterial strains of the DNAs on each of the filters of dot blot hybridization, and FIG. 1(b) shows the results obtained by color development after the hybridization process using each probe.

BEST MODE FOR CARRYING OUT THE INVENTION

In order to explain the present invention in more detail, non-limiting Examples with respect to the probes which are derived from Streptococcus pyogenes, causative bacteria of infectious diseases are shown below.

EXAMPLE 1

DNA Probe Derived from Streptococcus pyogenes
(1) Preparation of DNA probes derived from the bacteria Streptococcus pyogenes Clinical isolate of Streptococcus pyogenes was cultured overnight in BHI (Brain Heart Infusion) medium, then the cultured cells were harvested, and genomic DNA was extracted therefrom in accordance with Saito-Miura modified method ("Preparation of transforming deoxyribonucleic acid by phenol treatment", Biochem. Biophys. Acta vol. 72, pp.619–629 (1963)) in which cell lysis step was carried out by adding N-Acetylmuramidase SG to the lysis buffer.

The extracted DNA was completely digested with restriction enzyme HindIII, then random cloned into vector pGEM-3Z. Six probes specific to Streptococcus pyogenes, that is to say, the probes comprising DNA fragments which showed specific reactivities toward DNA included in natural Streptococcus pyogenes, were selected from thus obtained clones.

Thereafter, the selected probes were named: probe SP-6-28, probe SP-7-44, probe SP-14-1, probe SP-26-36, probe SP-26-46, and probe SP-55-3.
(2) Studies of species specificity of the DNA probes derived from Streptococcus pyogenes Interactions between each probes and DNAs from several kinds of causative bacterial strains of infections were studied as follows.

First, the clinical isolates and deposited bacterial strains as listed in Table 1 below were prepared. In order to obtain the sources of Human genomic DNA in Table 1 and a control sample, leucocytes which were collected from four healthy adult men, and *Escherichia coli* K-12, JM109 transformant containing plasmid pGEM-3Z were respectively prepared.

TABLE 1

| Bacteria No. | Abbrev. | Name | Origin |
|---|---|---|---|
| 1 | SP | *Streptococcus pyogenes* | Clinical Isolate |
| 2 | SAG | *Streptococcus agalactiae* | Clinical Isolate |
| 3 | SPN | *Streptococcus pneumoniae* | NYSDH DP-2 |
| 4 | SA | *Staphylococcus aureus* | ATCC 25923 |
| 5 | SE | *Streptococcus epidermidis* | ATCC 12228 |
| 6 | EC | *Escherichia coli* | ATCC 25922 |
| 7 | KP | *Klebsiella pneumoniae* | Clinical isolate |

TABLE 1-continued

| Bacteria No. | Abbrev. | Name | Origin |
|---|---|---|---|
| 8 | EBC | Enterobacter cloacae | Clinical Isolate |
| 9 | EF | Enterococcus faecalis | Clinical Isolate |
| 10 | PA | Pseudomonas aeruginosa | ATCC 27583 |
| 11 | HIN | Haemophills influenzae | Clinical Isolate |
| 12 | HUM | U937 Human Genomic DNA | |

Abbreviation
NYSDH: New York State Department of Health (Albany, N.Y., U.S.A.)

Thereafter, the DNAs included in each of the clinical isolates were extracted according to the method described in Example 1(1), then the aliquot of the extracted DNA (e.g., 10–100 ng) was spotted onto a nylon filter. After denaturation with alkali, the filter was subjected to dot blot hybridization. The human genomic DNA sample was prepared from the leukocyte obtained as mentioned previously using Saito-Miura modified method (supra). A control sample was prepared from *Escherichia coli* K-12, JM109 transformant containing plasmid pGEM-3Z using the method for preparation of plasmid DNA described in the following Example 2(1). Hybridization was then carried out overnight using a Digoxigenin-11-dUTP (BRL) labeled DNA probe which was derived from the *Streptococcus pyogenes* under a hybridization condition of 45% formamide, 5×SSC, at 42° C. according to Manual by Maniatis (T. Maniatis,et al., "Molecular Cloning (A Laboratory Manual Second Edition)"., Cold Spring Harbour Laboratory (1989)).

After overnight hybridization was completed, the samples were washed two times with 0.1×SSC, 0.1% SDS at 55° C. for 20 min. according to the manual, followed by color development and detection using Anti-Dig-ALP conjugates (BRL), thus results of hybridization were revealed. These results are shown in FIG. 1, wherein FIG. 1(*a*) illustrates the positions of the originated bacterial strains of the DNAs on each of the filters of dot blot hybridization, and FIG. 1(*b*) illustrates the results obtained by color development after the hybridization process using each of the above mentioned probes SP-6-28, SP-7-44, SP-14-1, SP-26-36, SP-26-46 and SP-55-3.

The experimental results with respect to the reactivities between each probes and DNAs from each of the clinical bacteria strains are shown in Table 2 below.

TABLE 2

| Bacteria | | | Probe (Denotation: SP-) | | | | | |
|---|---|---|---|---|---|---|---|---|
| No. | Abbrev. | Name | 6-28 | 7-44 | 14-1 | 26-36 | 26-46 | 55-3 |
| 1 | SP | *Streptococcus pyogenes* | + | + | + | + | + | + |
| 2 | SAG | *Streptococcus agalactiae* | − | − | − | − | − | − |
| 3 | SPN | *Streptococcus pneumoniae* | − | − | − | − | − | − |
| 4 | SA | *Staphylococcus aureus* | − | − | − | − | − | − |
| 5 | SE | *Staphylococcus epidermidis* | − | − | − | − | − | − |
| 6 | EC | *Escherichia coli* | − | − | − | − | − | − |
| 7 | KP | *Klebsiella pneumoniae* | − | − | − | − | − | − |
| 8 | EBC | *Enterobacter cloacae* | − | − | − | − | − | − |
| 9 | EF | *Enterococcus faecalis* | − | − | − | − | − | − |
| 10 | PA | *Pseudomonas aeruginosa* | − | − | − | − | − | − |
| 11 | HIN | *Haemophills influenzae* | − | − | − | − | − | − |
| 12 | HUM | U937 Human Genomic DNA | − | − | − | − | − | − |

Remarks
+: hybridization signal detected
−: hybridization signal not detected

As is evident from the Tables 1 and 2 above, all of the present probes showed reactivities only to the DNA derived from *Streptococcus pyogenes,* while no reactivity (i.e., hybrid formation) was observed toward the DNAs from the every other bacterial species in the genus Streptococcus, as well as the DNAs from the bacterial species other than genus Streptococcus. Thus, the specificity of the probes was demonstrated.

EXAMPLE 2

Analysis of the Base Sequence

Each of the base sequences of the DNA probes (six probes in total) of which species specificity was demonstrated in Example 1 as above was determined according to the following procedure.
(1) Preparation of Plasmid DNA

*Escherichia coli* K-12, JM109 transformant, wherein the sub-cloned insert fragment (to be sequenced) is contained in pGEM-3Z (Promega), was inoculated into 5 ml of Luria-Bactani Medium (bacto-tryptone, 10 g/1 L; bacto-yeast extract, 5 g/1 L; NaCl, 10 g/1 L; adjusted pH to 7.0 with 5N NaOH) and cultured overnight.

The culture liquid mixture was centrifuged (5,000 rpm, 5 min.) to collect the bacteria. One hundred μl of a solution of 50 mM glucose/50 mM Tris-HCl (pH8.0)/10 mM EDTA containing 2.5 mg/ml of lysozyme (Sigma) was added to the precipitate, and left at room temperature for 5 minutes. To the suspension, 0.2M NaOH solution containing 1% of sodium dodecyl sulfate (Sigma) was added and mixed. One hundred and fifty μl of 5M potassium acetate aqueous solution (pH 4.8) was further added thereto and mixed, then cooled on ice for 15 minutes.

The supernatant collected by centrifugation (15,000 rpm, 15 min.) of the mixture was treated with phenol/CHCl$_3$, and ethanol of two times by volume was added thereto, then the precipitate was again obtained by centrifugation (12,000 rpm, 5 min.). This precipitate was dissolved in 100 μl of a solution of 10 mM Tris-HCl (pH7.5)/0.1 mM EDTA, followed by addition of 10 mg/ml RNase A (Sigma) solution, then the mixture was left at room temperature for 15 minutes.

Three hundred μl of 0.1M sodium acetate aqueous solution (pH 4.8) was added to this mixture and treated with phenol/CHCl$_3$, then the precipitate was obtained therefrom by adding ethanol to the supernatant. This precipitate was dried and dissolved in 10 μl of distilled water to give a DNA sample.

(2) Pretreatment for Sequencing

Pretreatment for sequencing was performed with Auto-Read™ Sequencing Kit (Pharmacia).

Concentration of DNA to be employed as a template was adjusted to 5–10 μg in 32 μl of a solution. Thirty two μl of the template DNA solution was transferred to a mini-tube (1.5 ml, Eppendolf), and added thereto 8 μl of 2M NaOH aqueous solution, then mixed gently. After instant centrifugation, it was left at room temperature for 10 minutes.

Seven μl of 3M sodium acetate (pH 4.8) and 4 μl of distilled water were added, followed by 120 μl of ethanol, and after mixing, the mixture was left for 15 minutes on ethanol/dry ice. DNA which was precipitated by centrifugation for 15 minutes was collected, and the supernatant was removed carefully. The precipitate thus obtained was washed with 70% ethanol and centrifuged for 10 minutes. Then, after the supernatant was carefully removed again, the precipitate was dried under the reduced pressure.

The precipitate was dissolved in 10 μl of distilled water, then 2 μl of fluorescent primer (0.42 A$_{260}$ unit/ml, 4–6 pmol [Fluorescent Primer; Universal Primer: 5'-Fluorescein-d [CGACGTTGTAAAACGACGGCCAGT (SEQ ID NO: 7)]-3' (1.6 pmol/μl, 0.42 A$_{260}$ unit/ml); Reverse Primer: 5'-Fluorescein-d[CAGGAAACAGCTATGAC (SEQ ID NO: 8)]-3' (2.1 pmol/μl, 0.42 A$_{260}$ unit/ml), and 2 μl of annealing buffer was added thereto, and mixed gently.

After instant centrifugation, the mixture was heat-treated at 65° C. for 5 minutes and rapidly transferred to a circumstance of 37° C. and kept the temperature for 10 minutes. After keeping the temperature, it was left at room temperature for more than 10 minutes, and centrifuged instantly.

Then, the sample was prepared by adding thereto 1 μl of elongation buffer and 3 μl of dimethyl sulfoxide.

Four mini-tubes have been identified with one of the marks of "A", "C", "G" and "T", and, according to the respective mark, 2.5 μl of A Mix (dissolved ddATP with dATP, dCTP, c$^7$dGTP and dTTP), C Mix (dissolved ddCTP with dATP, dCTP, c$^7$dGTP and dTTP), G Mix (dissolved ddGTP with dATP, dCTP, c$^7$dGTP and dTTP), or T Mix (dissolved ddTTP with dATP, dCTP, c$^7$dGTP and dTTP) was poured into each identified tube. Each solution was preserved on ice until use, and was incubated at 37° C. for one minute or more before use.

Two μl of diluted T7 DNA polymerase (Pharmacia; 6–8 units/2 μl) was added to the DNA sample, and completely mixed by pipetting or mixing it gently.

Immediately after completion of the mixing, the mixed solution was distributed to 4.5 μl of the four types of the solutions respectively which had been incubated at the same temperature. Fresh tips were used for each distribution.

The solutions were kept for 5 minutes at 37° C., then 5 μl of termination solution was added to each reaction mixture.

Fresh tips were also used for this step. Immediately after incubating the solution for 2–3 minutes at 90° C., it was cooled on ice. Four to six μl of the solution per lane was applied for the electrophoresis.

(3) Sequencing on Base Sequences

Sequencing on the base sequences of the probes disclosed in Examples 1 and 2, having the specificity toward DNA from *Streptococcus pyogenes* was performed using A.L.F. DNA Sequencer System (Pharmacia) under a condition of the electrophoresis process of 45° C. for 6 hours. Primers were serially designed based on the sequences elucidated from each of the upstream and downstream sequences, and the above described procedures were repeated.

Consequently, all of the entire base sequences of the probe SP-6-28 (SEQ ID NO: 1), probe SP-7-44 (SEQ ID NO: 2), probe SP-14-1 (SEQ ID NO: 3), probe SP-26-36 (SEQ ID NO: 4), probe SP-26-46 (SEQ ID NO: 5) and probe SP-55-3 (SEQ ID NO: 6) were elucidated.

INDUSTRIAL APPLICABILITY

Using the probes according to the present invention, the causative bacteria which were incorporated into the phagocytes can be rapidly and accurately identified directly without proliferation of the bacteria by for example, a hybridization method. In other words, the diagnosis wherein the probes of the present invention are used enables the identification of the causative bacteria with single specimen, further, the necessary time for diagnosis can be diminished to approximately 1 to 2 days, while the conventional method with low detection rate requires 3–4 days, and the resulting detection rate is remarkably improved.

Therefore, the present invention provides guiding principles of the therapeutic treatment for the infectious diseases caused by *Streptococcus pyogenes*, in addition, the effective treatment in an early stage of the infection can be adopted to the patients, which may lead to a reduction of the mortality.

Additionally, in accordance with the present invention wherein the base sequences of the probes which specifically react with the DNA derived from *Streptococcus pyogenes* among other several causative bacteria of the infectious diseases were elucidated, artificial preparation of these probes has become feasible. Moreover, a part of the information of the base sequences provided herein may be utilized to produce primers, which are useful for rapid diagnosis through amplification of DNA of causative bacteria contained in the clinical specimen by a PCR method.

Furthermore, the rapid identification of the causative bacteria may be carried out by comparing the base sequences of the genomic DNA from the clinical specimen with the base sequences provided by the present invention.

As stated above, the present invention provides the desired probe for the diagnosis of the infections, besides, outstanding utilities as guiding principles for the manufacture of the primers for PCR as well as standard sequences which are suitable for the comparison of genomic DNA contained in the clinical specimen can be expected. Moreover, the present invention may exert beneficial effects by providing valuable clues for preparation and development of the novel probes which specifically react with the DNA from the causative bacteria of the infectious diseases.

Further, the base sequence disclosed in the present application was obtained by random-cloning of the genomic DNA from the clinical isolates, therefore, the utilities of the base sequences of the present invention should be encompassed to the complementary strand thereof.

Additionally, it may be presumed that DNA obtained from the wild strains might contain the mutated portion. However, as apparent from the disclosure of the Examples above, such mutated DNA portion would not affect the utilities which should be derived from the present invention, comprising the specificity of the probe of the present invention in the hybridization procedure for the diagnosis of the infections, and usages of the information on the base sequences disclosed in the present application for designing the primer to be employed for the PCR techniques with the aim of a rapid diagnosis of the infections.

We claim:

1. A purified nucleic acid useful as a probe for diagnosing infectious diseases consisting of a nucleotide sequence selected for the group consisting of SEQ ID NOS: 1, 2, 3, 4, 5, and 6, and the complements of SEQ ID NOS: 1, 2, 3, 4, 5, and 6.

2. A purified nucleic acid according to claim 3 consisting of the nucleotide sequence set forth in SEQ ID NO: 1, or the complement of SEQ ID NO: 1.

3. A purified nucleic acid according to claim 1 consisting of the nucleotide sequence set forth in SEQ ID NO: 2, or the complement of SEQ ID NO: 2.

4. A purified nucleic acid according to claim 1 consisting of the nucleotide sequence set forth in SEQ ID NO: 3, or the complement of SEQ ID NO: 3.

5. A purified nucleic acid according to claim 1 consisting of the nucleotide sequence set forth in SEQ ID NO: 4, or the complement of SEQ ID NO: 4.

6. A purified nucleic acid according to claim 1 consisting of the nucleotide sequence set forth in SEQ ID NO: 5, or the complement of SEQ ID NO: 5.

7. A purified nucleic acid according to claim 1 consisting of the nucleotide sequence set forth in SEQ ID NO: 6, or the complement of SEQ ID NO: 6.

8. A purified polynucleotide consisting of a nucleotide sequence selected from the group consisting of SEQ ID NOS: 1, 2, 3, 4, 5, and 6, and the complements of SEQ ID NOS: 1, 2, 3, 4, 5, and 6.

9. A probe for the diagnosis of infectious disease comprising a purified nucleic acid according to claim 1, said nucleic acid further comprising a detectable label.

10. A probe for the diagnosis of infectious disease comprising a purified polynucleotide according to claim 8, said polynucleotide further comprising a detectable label.

11. A purified nucleic acid useful as a probe for diagnosing infectious diseases consisting of a nucleotide sequence selected from the group consisting of SEQ ID NOS: 1, 2, 3, 4, 5, and 6, and the complements of SEQ ID NOS: 1, 2, 3, 4, 5, and 6, wherein said nucleic acid hybridizes to genomic DNA of *Streptococcus pyogenes*, but fails to hybridize to genomic DNA of *Streptococcus agalactiae* and *Streptococcus pneumoniae*, under the following hybridization and washing conditions: hybridization overnight at 42° C. in a hybridization solution comprising 45% formamide and 5×SSC; and washing twice for 20 minutes at 55° C., in a washing solution comprising 0.1×SSC and 0.1% SDS.

12. A purified nucleic acid according to claim 11 consisting of the nucleotide sequence set forth in SEQ ID NO: 1, or the complement of SEQ ID NO: 1.

13. A purified nucleic acid according to claim 11 consisting of the nucleotide sequence set forth in SEQ ID NO: 2, or the complement of SEQ ID NO: 2.

14. A purified nucleic acid according to claim 11 consisting of the nucleotide sequence set forth in SEQ ID NO: 3, or the complement of SEQ ID NO: 3.

15. A purified nucleic acid according to claim 11 consisting of the nucleotide sequence set forth in SEQ ID NO: 4, or the complement of SEQ ID NO: 4.

16. A purified nucleic acid according to claim 11 consisting of the nucleotide sequence set forth in SEQ ID NO: 5 or the complement of SEQ ID NO: 5.

17. A purified nucleic acid according to claim 11 consisting of the nucleotide sequence set forth in SEQ ID NO: 6, or the complement of SEQ ID NO: 6.

18. A purified polynucleotide useful as a probe for diagnosing infectious diseases consisting of a nucleotide sequence selected from the group consisting of SEQ ID NOS: 1, 2, 3, 4, 5, and 6, and the complements of SEQ ID NOS: 1, 2, 3, 4, 5, and 6, wherein said polynucleotide hybridizes to genomic DNA of *Streptococcus pyogenes*, but fails to hybridize to genomic DNA of *Streptococcus agalactiae* and *Streptococcus pneumoniae*, under the following hybridization and washing conditions: hybridization overnight at 42° C. in a hybridization solution comprising 45% formamide and 5×SSC; and washing twice for 20 minutes at 55° C., in a washing solution comprising 0.1×SSC and 0.1% SDS.

19. A probe for the diagnosis of infectious disease comprising the purified nucleic acid according to claim 11, said nucleic acid further comprising a detectable label.

20. A probe for the diagnosis of infectious disease comprising the purified polynucleotide according to claim 18, said polynucleotide further comprising a detectable label.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 3549 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes
        (B) STRAIN: Clinical Isolate SP-6-28

(xi) SEQUENCE DESCRIPTION: SEQ ID NO:1:

```
AAGCTTGTGC TGCTGCACCA CTAGCGTTTG AAAAATGAGT GTTAGTCATG CCTAATTGTT      60

TGGCTGTGGC ATTAATACGA TCGATAAACG CAGAAGCATC ATTGTTTGAT AAATAATTGG     120

CAATCATAAC AGTTGCTGCA TTTGATGAAG GCACAGCTGT CATAGTAATA AGATCACGAA     180

TAGGATAAGC TACTCCAGCG ACGATATTAT TATTGCTAAT CTCATAAATG TTAGCGATAG     240

CTTGATCGGT TGGAGTTGCC GTAATAGTAG TGTCCATCGT AATTTTTCCC TTAGCGAGCT     300

CTTCAAATAA AATGTAAAGC GTAAACATTT TAGACATACT AGCAGGATCC CTAGGAATAT     360

CAATATTATC TTGCCAAAGA ATATCTGAAC TATTTGCATC AACGACAATA GAAGATTTTG     420

GTCGATTAAC CTCACTAACT GTGTAGCCTG CTTGCCTTGT AATATCCATG ACATCTTCGG     480

CTTGGACAAG AGGCATCACC GAAAAGCAAA TAAAGGTAAA AATAGTTAGT ATAATTCTTT     540

TGGTCAATTT CCGACTCCTT TAAATGTAAT GCATTTTCAG TATATCACTT TGCTAATACA     600

ATGTGAAGTT TTTTTGAAAA ATTGTTAGGA TTGGCCTAGT TTGCTTAAAT AAAAATGAAA     660

AAGACTGCAG AAGTACTCTG TCAGTCAATG TCATACAAAA AGCATTGTGT TATTCTATAA     720

AGAGGTATTG ACATACCTCA CAAAACGGTT CCACCAGACC TTTAAAAAGA AACTTTTAGA     780

AATGTTTTTT TGAAGGATAA GATTGATAGA AGGAGGAGTA TCCAGATAAC CCTGTCCAAT     840

AAGATGTTTA TCTTGAAGGG TTGCTCTACC TAAGACTTGT CCCTTTGATA GAGGTGCGAT     900

CATTGTGGAT GATTTCTTAG TAATATGGAC GGTATTTTTG GTCTTTGTAT GTATTGGTTT     960

GATAAAAAAT AAACTATTTT GGGCTACAAG TTTGACAGTT TTTTCAGGAC TGTCTAAGAC    1020

AGATAACGTT TTTACTGGTT TATTATTTTC AATTAACTGG ACTTTTTGAA AATTAATTAA    1080

AAGGTACTGC AACAATTGAT TGGTTGTTTT AAATATAGCT AAATCATCCT CGTGGCTTTG    1140

ATCAGCATTT AAAACTACTG TAATAACCCT CATTTGATTT TCGACACTAG TAGCTACAAA    1200

AGAAGCACCG GCTTTTTTAG AATAACCAAC AAAAAGACCA TCCACGCCTT CTCGATAACA    1260

AGGCATGCCT TTAAGCATGT AATTATAACT GTAAATGGTT TGTCCATCAA AAATAGTGGA    1320
```

-continued

```
GGATTTGCTA GATAATTTCA GTACTTCTGG AAATTCTAAT AAGAGATGCC TGGCAATAAT    1380

AGCTAAATCA GTGGCGCAAA AACAATTTTC GTCATCTGGT TCTGTATTAG GATAAGTATT    1440

AGCTCCTAAA AAATGGTTAG TTAAGCCAGT TGAATTAACG ACCTTTGCAT CGGAAATGCC    1500

CCATTGCCTT AATTGTTTTT TCATTTTGTC AACAAATTTG GGTTCGGTTC CGCCTATTTT    1560

TTCAGCTAAA GCAATAGCGG GGCTATTGGC GTTATTAACA ACTAACGCAC TTAAAAGTTC    1620

TTTAACGGTA TATTTTCTCT TATCAAGAGG AACGTTACTA ATAGTATAGT TTGTAGTGAG    1680

TTCATAAGGG TAGTTAGAAA TAGTTACAGG ACTATCCCAA TTTAGCTTGC CCTTAGAAAC    1740

TTCTTTGTAA ACCAGATAGG TTGTCAAGAG CTTACTGACT GAGGCGACTG GGACAACCTT    1800

CTTTAGTATC TTTTTCGTAT AAAACTTTGC CACTTTCAAG GTCAACGGCA ATCGCATGCT    1860

TAGCAGTTAC CGAATACTCT TCACCGCTAA CAGTGCTTGC TGCAAAAAAT AAGGCGATGA    1920

CCACTAGGGA AATTAATCGT TTGATCATTT ATAGATTATC CTTACTCAAG TATTATTTTT    1980

TTAATTATAC CATATTTTTG TCTAAGGTAA TGACTTACCT CACAAGAGTA GTGATGCAAT    2040

AAAACGCTAC CATGAGAGAA TGACAATCTT TATTAAACTA ATTGAAACCT CATTAAAAAA    2100

GGGGTATAAC GCTTTCATAT AGATAAATGT ATAAAATAAA GAAAATTCTA CGAAATATTC    2160

AGATAATTTT TCATTTCATT ATTTTCTTTA AGAAAGTTTT ATGATATAAT GTCTTCAATT    2220

AACCAATTTC ATTTAGCAAT TGCCAAAAAA TGAAAATAAA GTTTAGGGGT GACTTTTATG    2280

AAGAAAAGTA AATGGTTGGC AGCTGTAAGT GTTGCGATCT TGTCAGTATC CGCTTTGGCA    2340

GCTTGTGGTA ATAAAAATGC TTCAGGTGGC TCAGAAGCTA CAAAAACCTA CAAGTACGTT    2400

TTTGTTAACG ATCCAAAATC ATTGGATTAT ATTTTGACTA ATGGCGGTGG AACGACTGAT    2460

GTGATAACAC AAATGGTTGA TGGTCTTTTG GAAAACGATG AGTATGGTAA TTTAGTACCA    2520

TCACTTGCTA AAGATTGGAA GGTTTCAAAA GACGGTCTGA CTTATACTTA TACTCTTCGC    2580

GATGGTGTCT CTTGGTATAC GGCTGATGGT GAAGAATATG CCCCAGTAAC AGCAGAAGAT    2640

TTTGTGACTG GTTTGAAGCA CGCGGTTGAC GATAAATCAG ATGCTCTTTA CGTTGTTGAA    2700

GATTCAATAA AAAACTTAAA GGCTTACCAA AATGGTGAAG TAGATTTTAA AGAAGTTGGT    2760

GTCAAAGCCC TTGACGATAA AACTGTTCAG TATACTTTGA ACAAGCCTGA AGCTACTGG     2820

AATTCAAAAA CAACTTATAG TGTGCTTTTC CCAGTTAATG CGAAATTTTT GAAGTCAAAA    2880

GGTAAAGATT TTGGTACAAC CGATCCATCA TCAATCCTTG TTAATGGTGC TTACTTCTTG    2940

AGCGCCTTCA CCTCAAAATC ATCTATGGAA TTCCATAAAA ATGAAAACTA CTGGGATGCT    3000

AAGAATGTTG GGATAGAATC TGTTAAATTG ACTTACTCAG ATGGTTCAGA CCCAGGTTCG    3060

TTCTACAAGA ACTTTGACAA GGGTGAGTTC AGCGTTGCAC GACTTTACCC AAATGACCCT    3120

ACCTACAAAT CAGCTAAGAA AAACTATGCT GATAATATTA CTTACGGAAT GTTGACTGGA    3180

GATATCCGTC ATTTAACATG GAATTTGAAC CGTACTTCTT TCAAAAACAC TAAGAAAGAC    3240

CCTGCACAAC AAGATGCCGG TAAGAAAGCT CTTAACAACA AGGATTTTCG TCAAGCTATT    3300

CAGTTGCTTT TGACCGAGCG TCATTCCAAG CACAAACTGC AGGTCAAGAT GCCAAAACAA    3360

AAGCCTTACG TAACATGCTT GTGCCACCAA CTTTTGTAAC CGTTGGAGAA AGTGATTTTG    3420

GTTCAGAAGT TGAAAAGGAA ATGGCAAAAC TTGGTGATGA ATGGAAAGAC GTTAACTTAG    3480

CTGATGCTCA AGATGGTTTC TATAATCCTG AAAAAGCAAA AGTTGAATTT GCAAAAGCCA    3540

AAGAAGCTT                                                           3549
```

(2) INFORMATION FOR SEQ ID NO:2:

```
    (i) SEQUENCE CHARACTERISTICS:
        (A) LENGTH: 3200 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes
        (B) STRAIN: Clinical Isolate SP-7-44

(xi) SEQUENCE DESCRIPTION: SEQ ID NO:2:

AAGCTTCAAA AATGGCTGGT CTAAAAAAAG TTCCAGCTAT CATCAAGAAG ATCTCTACAC      60

TCGAGAGTAT GCAACAAGCT ATAGTTGAAA ATTTACAACG TTCTAACCTT AACGCTATCG     120

AAGAAGCTAA AGCCTATCAG TTATTGGTTG AAAAAAAACA CATGACTCAC GATGAGATTG     180

CTAAATATAT GGGAAAATCA AGACCTTATA TTAGCAATAC CTTACGTCTG TTACAACTCC     240

CAGCACCTAT CATTAAAGCA ATTGAAGAAG GAAAAATTAG TGCGGGACAC GCGCGTGCTC     300

TTTTAACTTT GAGTGATGAT AAGCAACAAC TGTACCTCAC TCATAAAATA CAAAATGAAG     360

GCCTAAGTGT TAGGCAAATT GAGCAACTGG TTACTTCTAC TCCAAGTTCG AAGCTATCTA     420

AAAAAACTAA AAATATTTTT GCCACTTCTT TAGAGAAACA ATTGGCTAAA TCATTGGGAC     480

TCTCTGTCAA TATGAAGCTG ACAGCAAACC ATAGTGGGTA CCTTCAGATA TCTTTTTCCA     540

ATGATGATGA ATTAAACAGA ATTATCAACA AGCTACTTTA GCTTGTTGAT ATTCTGTTTT     600

TTCTTTTTTA GTTTTCCACA TGAAAAATAG TTGAAAACAA TAGCGGTGTC ACATTAAAAT     660

GGCTTTTCCA CAGGTTGTGG AGAACCCAAA TTAACAGTGT TAATTTATTT TCCACAGGTT     720

GTGGAAAAAC TAACTATTAT CCATCGTTCT GTGGAAAACT AGAATAGTTT ATGGTAGAAT     780

AGTGCTAGAA TTATCCACAA GAAGGAACCT AGTATGACTG AAAATGAACA AATTTTTTGG     840

AACAGGGTCT TGGAATTAGC TCAGAGTCAA TTAAAACAGG CAACTTATGA ATTTTTTGTT     900

CATGATGCCC GTCTATTAAA GGTCGATAAG CATATTGCAA CTATTTACTT AGATCAAATG     960

AAAGAACTCT TTTGGGAAAA AAATCTTAAA GATGTTATTC TTACTGCTGG TTTTGAAGTT    1020

TATAACGCTC AAATTTCTGT TGACTATGTT TTCGAAGAAG ACCTAATGAT TGAGCAAAAT    1080

CAGACCAAAA TCAATCAAAA ACCTAAGCAG CAAGCCTTAA ATTCTTTGCC TACTGTTACT    1140

TCAGATTTAA ACTCGAAATA TAGTTTTGAA AACTTTATTC AAGGAGATGA AAATCGTTGG    1200

GCTGTTGCTG CTTCAATAGC AGTAGCTAAT ACTCCTGGAA CTACCTATAA TCCTTTGTTT    1260

ATTTGGGGTG GCCCTGGGCT TGGGAAAACC CATTTATTAA ATGCTATTGG TAATTCTGTA    1320

CTATTAGAAA ATCCAAATGC TCGAATTAAA TATATCACAG CTGAAAACTT TATTAATGAG    1380

TTTGTTATCC ATATTCGCCT TGATACCATG GATGAATTGA AGAAAAATT TCGTAATTTA    1440

GATTTACTCC TTATTGATGA TATCCAATCT TTAGCTAAAA AAACGCTCTC TGGAACACAA    1500

GAAGAGTTCT TTAATACTTT TAATGCACTT CATAATAATA ACAAACAAAT TGTCCTAACA    1560

AGTGACCGTA CACCAGATCA TCTCAATGAT TTAGAAGATC GATTAGTTAC TCGTTTTAAA    1620

TGGGGATTAA CAGTCAATAT CACACCTCCT GATTTTGAAA CACGAGTGGC TATTTTGACA    1680

AATAAAATTC AAGAATATAA CTTTATTTTT CCTCAAGATA CCATTGAGTA TTTGGCTGGT    1740

CAATTTGATT CTAATGTCAG AGATTTAGAA GGTGCCTTAA AGATATTAG TCTGGTTGCT    1800

AATTTCAAAC AAATTGACAC GATTACTGTT GACATTGCTG CCGAAGCTAT TCGCGCCAGA    1860

AAGCAAGATG GACCTAAAAT GACAGTTATT CCCATCGAAG AAATTCAAGC GCAAGTTGGA    1920

AAATTTTACG GTGTTACCGT CAAAGAAATT AAAGCTACTA AACGAACACA AAATATTGTT    1980
```

```
TTAGCAAGAC AAGTAGCTAT GTTTTTAGCA CGTGAAATGA CAGATAACAG TCTTCCTAAA    2040

ATTGGAAAAG AATTTGGTGG CAGAGACCAT TCAACAGTAC TCCATGCCTA TAATAAAATC    2100

AAAAACATGA TCAGCCAGGA CGAAAGCCTT AGGATCGAAA TTGAAACCAT AAAAAACAAA    2160

ATTAAATAAC ATGTGGAAAA GAATATCTTT TATGAAATAG TTATCCACAA GTTGTGAACA    2220

ACCATTTAGT CTTGGATTCT CTCGTTTATT TAGAGTTATC CACTATATAC ACAAGACCTA    2280

CTACTACTAC TTATTATTAT ACTTATTAAA TAAAGGAGTT CTCATGATTC AATTTTCAAT    2340

TAATCGCACA TTATTTATTC ATGCTTTAAA TGCAACTAAA CGTGCTATTA GCACTAAAAA    2400

TGCCATTCCT ATTCTTTCAT CAATAAAGAT TGAAGTCACT TCTACAGGAG TAACTTTAAC    2460

AGGGTCTAAC GGTCAAATAT CAATTGAAAA CACTATTCCT GTAAGTAATG AAAATGCTGG    2520

TTTGCTAATT ACCTCTCCAG GAGCTATTTT ATTAGAAGCT AGTTTTTTTA TTAATATTAT    2580

TTCAAGTTTG CCAGATATTA GTATAAATGT TAAAGAAATT GAACAACACC AAGTTGTTTT    2640

AACCAGTGGT AAATCAGAGA TTACCTTAAA AGGAAAAGAT GTTGACCAGT ATCCTCGTCT    2700

ACAAGAAGTA TCAACAGAAA ATCCTTTGAT TTTAAAAACA AAATTATTGA AGTCTATTAT    2760

TGCTGAAACA GCTTTTGCAG CCAGTTTACA AGAAAGTCGT CCTATTTTAA CAGGAGTTCA    2820

TATTGTATTA AGCAATCATA AAGATTTTAA AGCAGTAGCG ACTGACTCTC ATCGTATGAG    2880

CCAACGTTTA ATCACTTTGG ACAAATACTT CAGCAGATTT TGATGTGGTT ATTCCAAGTA    2940

AATCTTTGAG AGAATTTTCA GCAGTATTTA CAGATGATAT TGAGACCGTT GAGGTATTTT    3000

TCTCACCAAG CCAAATCTTG TTCAGAAGTG AACACATTTC TTTTTATACA CGCCTCTTAG    3060

AAGGAAATTA TCCCGATACA GATCGTTTAT TAATGACAGA ATTTGAGACG GAGGTTGTTT    3120

TCAATACCCA ATCCCTTCGC CACGCTATGG AACGTGCCTT CTTGATTTCT AATGCTACTC    3180

AAAATGGTAC TGTTAAGCTT                                                3200

(2) INFORMATION FOR SEQ ID NO:3:

(i) SEQUENCE CHARACTERISTICS:
        (A) LENGTH: 5014 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Streptococcus pyogenes
         (B) STRAIN: Clinical Isolate SP-14-1

(xi) SEQUENCE DESCRIPTION: SEQ ID NO:3:

AAGCTTTTAA GGAGATTTCT TTAGATGCAT TCGTATCTGG TGTTGGTACT GGAGGAACAC      60

TTTCTGGTGT TCACATGTC TTGAAAAAAG CTAGCCCTGA AACTGTTATC TATGCTGTTG       120

AAGCTGAAGA ATCTGCTGTC TTATCTGGTC AAGAGCCTGG ACCACATAAA ATTCAAGGTA     180

TATCAGCTGG ATTATCCCA AACACGTTAG ATACCAAAGC CTATGACCAA ATTATCCGTG      240

TTAAATCGAA AGATGCTTTA GAAACTGCTC GACTAACAGG AGCTAAGGAA GGCTTCCTGG     300

TTGGGATTTC TTCTGGAGCT GCTCTTTACG CCGCTATTGA AGTCGCTAAA CAATTAGGAA     360

AAGGCAAACA TGTGTTAACT ATTTTACCAG ATAATGGCGA ACGCTATTTA TCGACTGAAC     420

TCTATGATGT GCCAGTAATT AAGACGAAAT AAAAAAGGGT TTGGAACTAC TAAGGTTCCA     480

GACTCTTTTT AGTGTTCTTT TTTAAAAACT GCAGGCTTTC TTCAATCCAC TGAGGTAACT     540

GCTCTTCAAG TGGCCTAAAG CCAATCTTGT GCCGACTGTT GGAATAACGA TGACGATGGA    600
```

```
AAAAATGCTG TTTTTCTTCT GCTAAGGTCC GCATAGATAA ACTTGGCTTT TTACTATATT      660

CATCAATATC AATTACTTGT ACTAAAACCT GGTTGCCTAT AGCCAATAAT TGATCAATAT      720

CGTCAATAAA TCCCGTTTTT ATTTCTGAAA TATGAATGAG ACCTGTTGTC CCATTTTCAA      780

GGGCAACAAA GGCTCCGTAT GGTTTAATCC CAGTGATGGT GCCATGCAGT TTGTCGCCAA      840

TTTTCATTAG TCAAATACCT CGATTGTTTC AATGATAACG TCTTCTTTAG GTTTATCCTG      900

TGCGCCAGTT TCAACGCCAG CAATCAAATC CAAAACTTGG AATGAAGTTT CGTCCACAAG      960

CTGACCAAAG ACCGTATGAC GACGATCAAG GTGAGGAGTT CCACCAATTG CAGCGTAAGA     1020

AGCTGCAATT GGAGCCGGCC AACCACCACG TTCTAGTTCT TTTTTGGCAT AAGGAATCTT     1080

ACTATTTTGA ACAATAAAGA ACTGACTGCC GTTAGTATTT GGTCCCGCAT TAGCCATCGA     1140

CAAGGCCCCA CGGAGATTAT AGAGTTCATC CGAAAATTCA TCTTCAAAAC TTTCACCATA     1200

GATGGATTGT CCACCCATTC CTGTTCCTGT TGGATCGCCC CCTTGAATCA TAAATTCAGG     1260

AATAATACGG TGGAAGATAA TCCCATCATA GTACCCTTCT TTAGCCAAAC CTAAGAAATT     1320

GGCTACTGTT TTAGGAGCAT GATCTGGGAA CAAGACCAGG GTCATATCGC CATGGTTTGT     1380

TTTAATGGTT GCTTTTGGTC CTTTATGGTT TGGCAAATCC AATTGTGGAA ACTGTAATTC     1440

TTTGTCAATC AATCCTAATT CCTCCAAGGC ATATAAAATG CCATCTTCTT TAACTTTTTT     1500

TGTGATAAAA TCTGCTTTTT CTTGCAGTAA TGGATGTGAT ACTCCCATTG CAATACTGAT     1560

ACCAGCATAG TCAATAACT CTAGGTCATT GAGTTCATCT CCAAAAACCA AAATGTTTTC     1620

AGGTTTTAAT CCTAAATGGT CAACTACTTT TGAAACACCT AGCGCTTTTG ACGTACCTTT     1680

CAAGACAACA TCTGATGAGT TATCGTGCCA TCTGACCAAA CGAAGGTGCT CTGCTAATTC     1740

AGCAGGCAAC TGCAAGCCAT CTCCCTTGTC CTCGAAAGTC CACATCTGGT AAACATCATG     1800

ATACTCATTA TAATCCGGAC AGACCTCTAG TTGAGCGTAG ACATTATCAA TAGCATTGCT     1860

AATCATGTCA TTTCGAGCGG ACAACACCGC TTCATGACGA CCCGCCATTC CATAAAAAAT     1920

GCCCATATCA TCCGCCCATT TTTTATAGGC CACAACAACA TCTGCTGGAA TCGGAGCTTG     1980

GAAAATAATA GTTTTAGCAT CGTCTTTGAC ATAAGCTCCA TTTAATTTGA CACAATAGTC     2040

AGCATGTAAA TCTTGAACTT CTTGTGGAAC ACCGTACCGA GCGCGACCTG AAGCAATACC     2100

AACCAAGATG CCTTTTGCCT TCAAAGCCTT AAATACTCTT TGAATCGACT CAGGCATATA     2160

ACCCGTATCT TTGACCCTCA AGGTATCATC AATATCAAAG AACACCATTT TGATTTTTTT     2220

AGCTTTGTAT TTTAGTTTTG CGTCCATACT TTCCTCCAAT TTGCTATACC CTATATTATA     2280

GCATTAATTA TCGTCTTGGG GGACTAAATG ATGTCGAAAA GCATAGACAA CCGCTTGGGT     2340

TCGGTCATCA ACTTCTAACT TGGCTAGAAT ATTGGACACA TGTGTTTTGA CGGTTTTTAA     2400

GGAAATAAAG AGTTCATCAG CGATGGTCTG ATTATCATAC CCTTTAGCTA AAAGGTGTAA     2460

AATATCATAC CCACGCGCTG TTAGTTCCTC ATGCAAGTCA GGGTGTTGAT CATGCGCCTT     2520

AATTTTTTTG TCAACTTCTG TTTCAATAGC TAACTCTCCC TTTGAAACCT TGCGAATGGC     2580

ATTTAAAATT TCAGCCGCAC TCGATGTTTT TAACATATAA CCCTTCGCTC CTGCATCAAT     2640

GACAGGGTAT ATCTTTTCAT TATCTAGATA GGAAGTTAAC ACAAGTACCT TAGCCTCTTT     2700

CCATTTTTTT AGAACTTCTA AAGTTGCCTC AACACCGCCT AACTCTGGCA TCACTAGATC     2760

CATAACCAAA ACATCTGGCT TCAAAGCCAA TGCCAAATCA ACCCCTTCAC GTCCATTAGA     2820

GGCCTCACCA ACGACATCAA TATCAGCTTG TAAATTCAAA AAACTCTTGA GTCCCATGCG     2880

GACCATTTCA TGATCATCGA CCAATATCAC TTTTATCTTA CTCATCGTCA TCTCCCTTCA     2940
```

```
CTATCGGCAG TCTAATATCC ATGGAAACTC CTTTGCCTTT TTGACTAATT AAATGTAGGT      3000

TTCCTGCTAA ATCATTGACA CGGTCTTCAA TATTCTTCAG ACCATAACTC AAATCCCTTA      3060

CCTGATCCAT ATCAAATCCT ACACCATCAT CAATCATCTT CAATTGTAAT TCTGTTGAGG     3120

TTTGATTGAG ATAAACTTCA ATTCGACTAG CTTTAGCATG TTTTAACGTG TTGCTAATGA      3180

ATTCTTGGGC AATTCTAAAA AGATTATCTT CCATTGTTTT AGGAAGCTGA GCAATGGTTT      3240

CCTTATAAAT GACTTCAATA TCACTTTTAT CTGTTAATTC CTAAGAATC ATATGAAGGC      3300

CCTCAGATAA AGTCCGATTA GCTAGCTCGG TAGGTCTAAG ATGCAAAAGG AGAATGCGTA     3360

GATCATTTTG AGCATTTTGC AACATTGCTT CAACCGTTGT TAACTGTGTT TGTAATTGTG     3420

TTTTGTCCAG TTGTTCCAAA CTCATTGAAA TTCCTGATAA AATCAATGAC GAAGCGAATA     3480

GCTCTTGACT GACTGTGTCA TGTAAATCTC TTGCAATTCG TTTGCGCTCT TGTTTTACAA     3540

CTTCTTGGCT ATCAAGAATA TAAGCACTTT CTTTCTTTTG CATGTTAGCA GTCAGGTGAG     3600

ACATTTTTTT AGAAAGTCGA CTTAAATTAG TATTGATTTC TGATGTCTCA TCTAGATAGA     3660

GTCGTCGATT ATTGAGAATA TATTTTAGAT TTTGGTTGAT GTTACGCTTA CTGTTATCAT      3720

CCATAATAAT CCACAATAAC AACAATAATA AAGTCACAGA AACAATCAAC AATAAAATCG     3780

AAAACCCTAG ACGTTCGACC TGCCATAAAT GATTGCGAAG GTAGTTAAAA GTGATTCCTA     3840

AATTATCCAT GACCACAAAA ACAATAGATA AAATGGTAAT GGTTGAGTAG AGCCAAACAA     3900

GAGCATAGTA ACGTTTTTTC ATCGCCTATC CACCTCAACA TTTCCGGCAA TAGTTGTAAC     3960

GATAATTTTG ACTTTTTTAA GGGATTGGTT ATCCGTTTCT TTTAACTTAA TAGATTCGTT     4020

GCGCAAATCA TATTGCTGAC ATCTAAAAAA ATCAACACTT CCGTATATGG AACTAACATC     4080

TAAAGTAACA GTGACATCAA TAGGTACCAA TATAGTCGTA TTTCCAAAAA TTTTACGTAT     4140

CACAATGATA TTATCCATTC CTGTCACAAT AACATTGGTT AAGTCAACCG TGTCATTTCC     4200

TGAGATTCGA ATGATGTTAA TGTCATCAAA ACAATAATAA TCACTTTCAT AATTAGCAGT     4260

ACCAATCCAT TGATGCTTGG TATTGTTCAC TTCAATCTTT TCTTCCTTGA AACGAATCAA     4320

GGCAAAGCGA TTCTTCTTTT TGACTTGTGA AAAATGGTTA ATGAAAATGT AAACTATCCC     4380

CAAAAGAACA GCCATGATAA TGTAGGGATT AAGCATGAAA ATTAAAAAAA GAAACAATAA     4440

ACTGACAGTT AGTAAAAAAT TATTGCGGCT ATCTTGGTTA TAAAAGCGTA ATGCTAATAA     4500

GATAAGAACT AGAATTAGGA TAAAACTTGA TAAATCATTA TCCAAGATTG TCATGATACC     4560

CATAGCTAGC AGTATACACT CGATAAGTAA AAAGAATTGA AATTTTTTCA TTAGTTTCCC     4620

CTTATTTCTT TGTATTTTAT CAGAATTCCT GGAAAATTGC ATCTTTATAT GACGAGTAGT      4680

TAAAAAGAAT AGTTAGTGGC ATGCTAGTAA AACATGAGAC TAACTATTCT TTGTTAAGGT     4740

GTTTGAGCAG TAGTTTCTGA TGGGCTTAAT TCAGTGTTGC TACCTGGTGC AGTACTATCA     4800

TTTGTTGAAG AACTGTTTGA ACTTGACGTT GAACTCGATG AGCTACTAGA AGAGTGTGTT     4860

TCTTCTGGAT AAAGGTAAAG ACTAATCTCT CCTTTATCAG ACAGACTCAA AGACGTTCCA     4920

TAGTAAGGAG ATTGACCACT GACAATAGCT TTAGAACTAG GAGAATGAAT TGGCACAAAG     4980

CCCGTTGCTG AGCTAGAGCT TGGCACATAA GCTT                                 5014
```

(2) INFORMATION FOR SEQ ID NO:4:

(i) SEQUENCE CHARACTERISTICS:
        (A) LENGTH: 7143 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Streptococcus pyogenes
    (B) STRAIN: Clinical Isolate SP-26-36

(xi) SEQUENCE DESCRIPTION: SEQ ID NO:4:

```
AAGCTTCGCC CTCAAGCCCT TTTTTTCCAA AGGTGGTTTT GTCTCAGTAC CGCCAGTTGT      60
GGCTGCTAAA TTGCTTGGTA AACCAGTCTT TATTCATGAA TCAGATCGGT CAATGGGACT     120
AGCAAACAAG ATTGCCTACA AATTTGCAAC TACCATGTAT ACCACTTTTG AGCAGGAAGA     180
CCAGTTGTCT AAAGTTAAAC ACCTTGGAGC GGTGACAAAG GTTTTCAAAG ATGCCAACCA     240
AATGCCTGAA TCAACTCAGT TAGAGGCGGT GAAAGAGTAT TTTAGTAGAG ACCTAAAAAC     300
CCTCTTGTTT ATTGGTGGTT CGGCAGGGGC GCATGTGTTT AATCAGTTTA TTAGTGATCA     360
TCCAGAATTG AAGCAACGTT ATAATATCAT CAATATTACA GGAGACCCTC ACCTTAATGA     420
ATTGAGTTCT CATCTGTATC GAGTAGATTA TGTTACCGAT CTCTACCAAC CTTTGATGGC     480
GATGGCTGAC CTTGTAGTGA CAAGAGGGGG CTCTAATACA CTTTTTGAGC TACTGGCAAT     540
GGCTAAGCTA CACCTCATCG TTCCTCTTGG TAAAGAAGCT AGCCGTGGCG ATCAGTTAGA     600
AAATGCCACT TATTTTGAGA GAGGGGCTA CGCTAAACAA TTACAGGAAC CTGATTTAAC     660
TTTGCATAAT TTTGATCAGG CAATGGCTGA TTTGTTTGAA CATCAGGCTG ATTATGAGGC     720
TACTATGTTG GCAACTAAGG AGATTCAGTC ACCGGACTTC TTTTATGACC TTTTGAGAGC     780
TGATATTAGC TCCGCGATTA AGGAGAAGTA AATGGCAAAA GATAAAGAGA AACAAAGTGA     840
TGACAAGCTC GTTTTGACAG AGTGGCAAAA GCGTAACATT GAATTTTTAA AGAAAAAGAA     900
GCAGCAAGCT GAGGAAGAAA AAAAACTCAA AGAGAAATTA TTGAGTGATA AAAAAGCGCA     960
CAGCAAGCTC AAAATGCTTC TGAAGCAGTT GAGCTTAAAA CTGATGAGAA AACTGATAGT    1020
CAGGAAATTG AGTCAGAAAC GACGTCAAAA CCTAAAAAAC CCAAAAAAGT TAGACAACCC    1080
AAGGAAAAAA GCGCGACACA AATCGCTTTT CAAAAATCCT TGCCTGTTCT TTTGGGGGCG    1140
CTCTTACTTA TGGCGGTGTC TATTTTTATG ATCACTCCTT ATAGCAAAAA GAAAGAGTTT    1200
TCTGTAAGAG GAAACCATCA AACGAACCTT GACGAATTAA TCAAAGCTAG CAAAGTCAAA    1260
GCATCTGACT ATTGGTTAAC GTTGTTAACT TCGCCTGGTC AGTATGAACG ACCGATTCTT    1320
CGTACTATTC CATGGGTGAA ATCTGTACAT CTCTCTTACC AATTTCCTAA TCACTTTCTA    1380
TTTAACGTTA TTGAATTTGA AATCATCGCT TATGCACAAG TCGAAAACGG TTTTCAGCCT    1440
ATTTTGGAGA ATGGAAAACG TGTGGACAAG GTCAGGGCAT CAGAACTACC GAAATCTTTC    1500
TTGATTCTTA ATTTAAAAGA TGAGAAAGCG ATCCAACAGT TAGTTAAGCA ATTAACGACA    1560
TTACCTAAAA AATTAGTCAA GAATATCAAG TCAGTGTCTC TTGCAAATTC CAAAACGACA    1620
GCGGATTTAC TACTTATTGA AATGTATGAC GGTAATGTAG TTAGAGTACC GCAGTCACAA    1680
CTCACATTGA AACTTCCCTA TTATCAAAAA TTGAAAAAAA ACCCTTGAAA ATGATAGTAT    1740
AGTGGATATG GAAGTTGGAA TTTACACTAC AACACAGGAG GATTGAAAAT CAACCTGAAG    1800
TTCCTCTTAC GCCAGAACAA AACGCAGCTG ATAAAGAAGG AGATAAGCCT GGTGAGCATC    1860
AGGAACAGAC AGACAATGAT TCAGAAACGC CAGCAAATCA GAGTAGTCCT CAGCAAGCAC    1920
CACCATCCCC AGAAACGGTC CTCGAACAGG CCCATGGCTA GCTAATATCT AAGTTGAAAA    1980
AGCAATGAAA ACGTTAGAAA TTCAACGATT CTAACCCATA ATGAATTGCC TAAAAAAAAT    2040
TAAGTTTATA TAACAAAAAA CGTAAAATGA TAACATTTTA CGTTTTTTTA TGGTATAATA    2100
TTTTCTGAAT GATTCTGTTT TTTAGCAGTT TTTAGAATAG CAAAAGTTTG GAAAGTAAGT    2160
```

```
GAGGTCAAGT GAATGGCTAG AAATGGCTTT TTTACTGGTT TGGACATTGG AACAAGCTCG    2220

ATAAAAGTTT TAGTAGCAGA ATTTATTTCT GGTGAGATGA ACGTCATTGG TGTTAGTAAT    2280

GTTCCAAGTA CCGGCGTAAA GATGGCATAA TAATCGATAT AGAGGCAGCT GCGACTGCCA    2340

TCAAAACTGC GGTAGAACAA GCAGAAGAAA AGCAGGGAT GACAATTGAA AAGGTTAATG     2400

TTGGGCTACC GGCAAACCTT CTTCAAATTG AACCAACACA AGGAATGATT CCTGTCCCAA    2460

GTGAGTCTAA AGAGATAAAA GATGAGGATG TTGATAGCGT TGTTAAATCG CTTTAACAA     2520

AAAGTATCAC ACCAGAACGA GAGGTTATCT CTTTAGTTCC AGAAGAGTTC ATTGTGGATG    2580

GCTTTCAGGG CATTCGAGAT CCACGTGGTA TGATGGGGAT TAGATTAGAG ATGCGCGGGC    2640

TTATTTATAC TGGACCAAGC ACAATTTTAC ATAATCTGCG TAAAACGGTA GAAAGAGCAG    2700

GCATTAAAGT TGAAAACATC ATTATTTCTC CGTTAGCTAT GGCTAAAACC ATTTTAAACG    2760

AAGGTGAGCG CGAGTTTGGA GCTACTGTAA TTGATATGGG AGGTGGACAG ACAACTGTCG    2820

CTTCTATGCG AGCACAAGAA TTGCAGTATA CCAATATATA TGCTGAAGGC GGCGAATACA    2880

TTACTAAAGA TATATCAAAA GTATTAAAAA CGTCTTTGGC TATTGCAGAA GCACTTAAGT    2940

TTAATTTTGG TCAAGCGGAG ATATCAGAAG CTAGTATAAC TGAAACAGTA AAAGTTGATG    3000

TGGTAGGTAG TGAAGAGCCT GTTGAGGTAA CTGAACGTTA TTTTATCTGA AATTATTTCC    3060

AGCGCGTATT CGTCATATTT TAGATCGTGT GAAGCAAGAT TTGGAAAGAG GTCGTTTACT    3120

AGACTTACCA GGAGGCATTG TTTTGATTGG TGGCGGTGCA ATCATGCCTG AGTGGTAGA    3180

AATTGCACAA GAAATCTTTG GAGTAACTGT AAAGCTCCAT GTTCCAAATC AAGTCGGTAT    3240

TAGAAATCCA ATGTTTTCAA ACGTTATCAG TTTGGTAGAA TATGTTGGTA TGATGTCTGA    3300

AGTAGACGTT TTAGCACAAA CTGCAGTTTC AGGAGAAGAA CTTTTGCGAC GCAAGCCTAT    3360

CTATTTCAGT GGTCAAGAAT CTTATTTACC AGATTATGAT GATTCAAGAA GACCAGAATC    3420

GACCATTGGC TATGAACAAC AAGCGTCACA ACAGCATAT GATTCACAAG TTCCGAGTGA     3480

TCCTAAACAA AAAATTTCAG AACGTGTTCG TGGCATATTT GGGAGTATGT TTGATTAAAA    3540

GTAATAAAGT GAGGAGATAA AATGGCGTTT TCATTTGATA CTGCATCAAT TCAAGGTGCA    3600

ATTATAAAAG TAATTGGAGT CGGCGGAGGT GGCGGAAATG CCATTAATCG TATGATTGAT    3660

GAAGGTGTTG CTGGTGTCGA GTTCATCGCA GCAAATACAG ACATTCAGGC ATTAAGCTCA    3720

TCAAAAGCTG AAACGGTTAT TCAACTAGGC CCTAAATTAA CTCGTGGACT TGGTGCTGGA    3780

GGACAACCTG AAGTAGGACG TAAAGCTGCT GAAGAAAGCG AAGAAATTTT AACAGAAGCT    3840

CTTACAGGAG CGGATATGGT ATTTATTACT GCCGGTATGG GTGGTGGCTC TGGGACAGGG    3900

GCTGCACCGG TTATTGCTCG TATCGCTAAG AGTTTGGGAG CCTTGACAGT AGCTGTTGTT    3960

ACTCGCCCGT TTGGTTTTGA AGGTAACAAA CGTGGTAATT TTGCTATTGA AGGTATCGAA    4020

GAACTCCGTG AACAAGTTGA TACTTTGTTA ATTATTTCAA ATAATAACCT TCTTGAGATT    4080

GTTGATAAAA AGACACCTTT ATTAGAAGCA CTTAGTGAAG CTGATAATGT TTTACGTCAG    4140

GGAGTTCAAG GGATAACCGA CTTAATTACT AGTCCTGGCC TTATCAATCT CGATTTTGCC    4200

GACGTGAAAA CAGTTATGGC AAATAAAGGG AATGCCTTAA TGGGATTGG GATTGGTTCT     4260

GGAGAAGAGC GCATTGTTGA GGCGGCGCGT AAGGCAATCT ATTCACCCCT ATTAGAAACG    4320

ACTATTGATG GTGCACAAGA CGTTATTGTG AACGTTACAG GAGGTCTCGA CATGACACTC    4380

ACAGAAGCTG AAGAAGCCTC TGAAATTGTT GGGCAAGCTG CTGGTCAAGG CGTTAACATT    4440

TGGTTAGGAA CATCTATTGA TGATACTATG AAAGATGACA TCCGTGTGAC TGTTGTAGCA    4500
```

```
ACTGGAGTGC GCCAAGAAAA AGCCGAACAA GTTTCAGGTT TTCGTCAGCC TAGGACTTTT  4560
ACCCAAACCA ACGCGCAGCA AGTAGCGGGT GCACAATATG CATCAGATCA AGCAAAACAG  4620
TCGGTTCAAC CAGGGTTTGA TCGTCGCTCA AATTTTGATT TTGACATGGG GGAGTCTCGC  4680
GAGATACCAA GTGCACAAAA GGTAATTTCT AATCATAATC AAAATCAAGG TTCTGCTTTT  4740
GGAAATTGGG ATTTGAGACG TGATAATATT TCTCGTCCAA CAGAAGGTGA ATTGGATAAC  4800
CATCTTAATA TGTCAACGTT CTCAGCTAAC GATGACAGTG ATGATGAATT AGAAACGCCT  4860
CCATTCTTTA AAACCGTTA ATAATGGATT TACTGACAAA TAAAAGAAA ATTTTTGAGA  4920
CTATCCGCTT ATCTACAGAG GCAGCAAATA GGACTAATGA TAGTGTTTCA GTTATTGCTG  4980
TAACAAAATA TGTGGATAGT ACAATTGCAG GTCAGCTTAT CGAAGCAGGA ATTGAGCACA  5040
TTGCCGAAAA CCGTGTTGAT AAATTTCTTG AAAAGTATGA TGCGTTAAAG TATATGCCAG  5100
TAAAGTGGCA TTTAATCGGT ACCTTACAAC GTCGTAAAGT CAAGGAAGTT ATCAATTATG  5160
TTGATTATTT TCACGCTCTA GATTCTGTGA GATTAGCTTT GGAAATCAAC AAGAGAGCTG  5220
ACCATCCTGT GAAGTGTTTT CTACAAGTTA ATATTTCTAA AGAAGAGAGT AAACATGGTT  5280
TTAACATTTC TGAGATTGAT GAAGCGATTG AAGAAATAGG TAAGATGGAG AAGATACAGT  5340
TAGTTGGTTT AATGACTATG GCACCAGCAA ATGCCAGTAA AGAAAGTATT ATAACTATTT  5400
TTCGACAAGC AAATCAATTA AGAAAAAACT TGCAGTTAAA AAAAAGAAAG AATATGCCTT  5460
TTACAGAATT GAGCATGGGC ATGAGTAACG ATTATCCAAT TGCTATTCAA GAAGGCTCAA  5520
CTTTTATTCG GATTGGTAGA GCTTTCTTTC ACTAATGGAG AATAAGATGG CTTTTAAAGA  5580
TACATTTAAC AAGATGATTT CTTATTTTGA CACGGATGAG GTTAACGAAG TTGAAGAAGA  5640
TGTTGCAGCA TCAACTGATA ACGTTATTCC AAGATCACAA CAATCAGTCA GAGCAAGTAG  5700
TCATCCAAAA CAAGAACCTA GAAACAATCA CGTACAACAA GATCATCAGG CGAGATCCCA  5760
AGAACAGACA AGGTCACAAA TGCATCCAAA ACATGGTACT TCTGAACGCT ATTATCAGCA  5820
GTCTCAGCCA AAAGAAGGCC ATGAAATGGT TGACAGAAGA AAACGGATGA GCACTTCTGG  5880
TATTGCAAAT CGCCGTGAGC AGTATCAACA ATCAACTTGT TCAGATCAGA CAACTATTGC  5940
CTTAAAATAT CCTCGTAAAT ATGAGGATGC TCAAGAAATT GTGGATCTTT AATAGTTAA  6000
TGAATGCGTT TTGATTGATT TTCAGTTTAT GCTAGATGCT CAGGCTAGAC GGTGTTTAGA  6060
TTTTATTGAT GGTGCTAGTA AAGTGCTCTA TGGTAGCTTA CAAAAGGTCG GCTCTTCAAT  6120
GTACTTACTG GCTCCGTCAA ATGTATCCGT CAATATAGAA GAAATGACTA TCCCACATAC  6180
TACACAAGAT ATTGGCTTTG ATTTTGATAT GAAAAGGCGG TAAATAAATG ATATTAATAC  6240
TATCTATTCT TCTTCGTCTG ATCAAAGTTT ACACTTATTT ATTGATTTTA CGCATTAATG  6300
TCATGGTTTC CTGGGGCATA TGATTCAAAA ATTGGGCGTT TGATTAGTGG TATCGTTGAA  6360
CCAATTTTAA AACCTTTTAG AGCATTTAAT TTACAATTTG CCGGTCTTGA CTTCACTATT  6420
TTTGTCGTCA TTATTAGTTT GAATTTTTTA GCTCAAGTTT TGGTCCGTGT GTTTATTTAA  6480
TGGTTAGTCA TAGTAAGATT TATCAGCATT TTCACCAAGA AGAATATCCT TTATTGATA  6540
GAATGTCTGA TATGATTAAT AGAGTTGGAG ATTACTATCT TTTAGAAGTT ACTGAGTTTT  6600
TAAATCCTAG AGAAGTGATG ATTTAAAAA GTTTGATTGC TTTAACAGAT CTAAAAATGT  6660
TCGTATCAAC AGATTACTAC CCAAGCGAAT ATGGTCGTGT CATTATTGCA CCTGGTTACT  6720
ATGACTTAGA ACAAAGTGAT TTTCAAATAG CTTTAGTAGA GATAAGTTAT CAGGCAAAGT  6780
TTAATCAGTT GACACATAGT CAAATTTTAG GAACTTTAAT TAATGAATTA GGAGTAAAGC  6840
GAAATTTATT TGGAGATGTT TTTGTTGAAA TGGGATATGC CCAGCTCATG ATTAAGCGGG  6900
```

-continued

```
AGTTATTGGA TTATTTTTTA GGAACAATTA CTAAAATAGC TAAAACTAGT GTGAAATTAA    6960

GAGAAGTTAA CTTTGATCAG TTAATTAGGT CTATTGATAA CAGCCAGACC CTGGATATTC    7020

TAGTTTCTAG TTTTCGATTA GATGGTGTAG TTGCTACTAT CTTAAAAAAA TCTCGAACGC    7080

AAGTTATAGC ATTAATTGAA GCAAATAAGA TTAAGGTAAA CTATCGACTC GCTAATAAAG    7140

CTT                                                                  7143
```

(2) INFORMATION FOR SEQ ID NO:5:

(i) SEQUENCE CHARACTERISTICS:
        (A) LENGTH: 6688 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes
        (B) STRAIN: Clinical Isolate SP-26-46

(xi) SEQUENCE DESCRIPTION: SEQ ID NO:5:

```
AAGCTTCATA TTTTGTTTGG TGCGATCGAC ACCAAGCCTA TTGCGGATAT GTTGGTTGCT      60

CTTGAGCAAA TAGGTGACTT GCAGGTTACT GGCTTTCATT ACCCTAACGC CTATCCATTG     120

GAAAAATACC CAGAACGTTT TGGTAGGGTT GCTGATTTCA AAGATTTCTT GGCCCTGCGT     180

AAGCATGCCA AAGCAGATGA CTTTTTCGTG ATTACAGGGT CGCTATATTT TATTTCAGAA     240

ATTAGACAGT ATTGGAAAAA ACATATTGAA AAAACGTTC TTTTAACCCA TTAAAAAAGA      300

GAAAATGAAA AGGAAAAGGA AAAAACTAAT GAAAAGGGAA AGACTAATGT CTATTAATAA     360

GGAAAAAGCA GAAGCAGCCA TTTATCAGTT TTTAGAGGCT ATTGGTGAAA ATCCAAATCG     420

GGAAGGTCTT CTTGACACGC CTAAACGGGT TGCTAAAATG TATGCGGAGA TGTTTTTGGG     480

ACTGGGAAAA GATCCTAAAG AGGAGTTTAC GGCTGTCTTT AAAGAACAAC ATGAGGATGT     540

GGTGATTGTC AAAGACATTA GTTTTTATTC TATATGTGAA CACCACTTAG TTCCTTTTTA     600

TGGCAAGGCT CATATCGCTT ACTTGCCAAG TGATGGTCGA GTAACAGGTT TGAGTAAATT     660

AGCGCGAGCA GTTGAAGTAG CTAGTAAACG ACCTCAACTC CAAGAGCGTT TGACCTCTCA     720

AATAGCGGAT GCTTTAGTTG AAGCCCTCAA TCCTAAAGGG ACTTTAGTTA TGGTAGAAGC     780

AGAGCACATG TGCATGACCA TGCGAGGCAT CAAAAAGCCA GGTAGTAAAA CCATTACCAC     840

CACTGCCAGA GGCTTATATA AGGAAAGTCG TGCTGAGAGG CAAGAAGTTA TTTCTCTAAT     900

GACAAAAGAT TAGGAGAACT TATGAAAATT GGAAAGTTTG TGATTGAGGG CAATGCGGCT     960

ATCATGGGGA TTTTAAATGT GACTCCAGAT TCTTTTTCAG ATGGGGGGTC TTACACTACT    1020

GTGCAAAAAG CATTAGATCA CGTTGAGCAA ATGATTGCTG ATGGGGCTAA AATCATCGAC    1080

GTTGGTGGAG AATCAACACG TCCAGGTTGC CAATTTGTAA GCGCTACCGA TGAAATTGAC    1140

CGGGTGGTTC CTGTGATCAA GGCCATCAAA GAAAACTATG ATATTCTAAT CAGCATTGAT    1200

ACCTATAAAA CCGAAACAGC TAGAGCAGCT TTAGAGGCGG GTGCCGATAT TCTCAATGAT    1260

GTTTGGGCAG GTTTGTACGA CGGTCAAATG TTTGCCTTAG CAGCCGAGTA CGATGCGCCT    1320

ATCATCTTGA TGCATAACCA AGACGAAGAA GTTTATCAAG AGGTAACACA AGACGTTTGT    1380

GATTTTCTAG GCAATAGAGC ACAAGCAGCT CTTGATGCTG GCGTGCCAAA AACAATATT     1440

TGGGTTGATC CAGGATTTGG ATTTGCCAAA TCTGTTCAAC AGAATACGGA GTTATTAAAA    1500

GGATTGGACC GCGTCTGTCA TTTGGGCTAT CCTGTCTTGT TTGGTATTTC GAGAAAGCGT    1560
```

-continued

```
GTCGTAGATG CCTTGTTAGG CGGAAACACC AAAGCTAAAG AGCGAGACGG AGCGACAGCA    1620

GCCTTGTCTG CTTATGCCCT TGGAAAAGGC TGTCAGATTG TACGCGTACA CGATGTCAAG    1680

GCTAATCAAG ACATTGTGGC TGTGTTGAGC CAGTTGATGT GAGGACTTAT GGATAAAATC    1740

GTATTAGAAG GTTGCCGTTT TTATGGCTAC CATGGAGCCT TTAAAGAAGA ACAGACCCTT    1800

GGGCAAATTT TTCTGGTTGA TTTAGAATTG TCAGTCGATT TGCAAGCAGC TTCTTTGTCA    1860

GACCAATTAA CAGATACGGT CCATTACGGG ATGGTGTTTG ATAGTGTCCG TCAGTTAGTG    1920

GAAGGGGAAA AGTTTATTTT GATTGAACGT TTAGCAGGTG CGATTTGTGA ACAGCTTTTT    1980

AACGAATTTC CGCCTATTGA AGCCATCAAA GTGGCCATTA AAAAGGAAAA CCCACCGATT    2040

GCAGGCCACT ATAAGGCAGT TGGTATTGAA TTGGAGAGAC AGAGATGACC ATTGTTTATT    2100

TAAGTTTAGG CACCAATATG GGGGACCGAG CAGCTTACTT GCAAAAAGCT CTTGAGGCTT    2160

TAGCTGACTT ACCTCAAACA CGGTTGCTTG CTCAATCATC CATTTATGAA ACGACTGCTT    2220

GGGGCAAGAC AGGCCAGGCT GATTTTCTCA ATATGGCCTG TCAATTAGAT ACACAATTAA    2280

CCGCGGCTGA TTTCTTAAAA GAAACACAAG CTATTGAGCA ATCTCTTGGT CGTGTGAGGC    2340

ATGAAAAATG GGGATCAAGA ACTATTGACA TTGATATCTT GCTATTTGGA GAAGAGTTTT    2400

ATGACACAAA GGAATTGAAA GTGCCACACC CTTATATGAC TGAGCGTGCT TTTGTTTTAA    2460

TCCCCTTATT GGAATTGCAG CCAGATTTAA AATTGCCTCC TAATCATAAG TTTTTAAGGG    2520

ATTATCTTGC AGCTTTAGAT CAATCAGATA TCACGCTCTT TTCAGCTCAA CAGACAGAGT    2580

TCTAGACTCT GTTTTCGGAG TAATGCCTGC TATAAGCCAA TCCATAAAGT TTTGCCAAAT    2640

TCATCGTTAT TTTTTCTAAA ATTTGATATA ATAGTATCGG CTTTATGCCG ATTTTTTTAC    2700

GCGTATAAGA AGTGATAAAA GAAAGAAGAT AACTATGATA ACTGAACTTC ATGGGATTGA    2760

TATTCGAGAG AATGAACCCC TAAAACATTA CACTTACACT AAGGTAGGTG CCCAGCAGA    2820

TTTCTTGGCT TTTCCTAGAA ATCACTACGA GCTATCACGC ATCGTTGCTT ATGCCAACAA    2880

AGAAAATATG CCTTGGCTTG TTTTGGGAAA TGCCAGCAAT CTCATTGTGC GAGATGGTGG    2940

TATTCGTGGC TTTGTCATCA TGTTTGATAA GCTAAATGCA GTGCACTTAA ATGGTTATAC    3000

CTTAGAAGCC GAAGCTGGTG CCAATCTGAT TGAAACAACG AAGATTGCCA AATTCCATAG    3060

TTTAACAGGG TTTGAATTTG CATGTGGCAT TCCTGGAAGC ATTGGGGGTG CTGTTTTTAT    3120

GAATGCGGGT GCCTATGGTG GGAAATATC ACATATTTTC TTATCCGCTA AGGTGCTTAC    3180

CTCAAGTGGA GAGATCAAAA CCATTTCAGC TAGGGATATG GCTTTTTGGT TACCGTCACT    3240

CTGCCATTCA AGAAACAGGT GACATTGTCA TTTCTGCTAA GTTGCTCTT AAACCGGGTA    3300

ATTATGATAC GATCAGCCAA GAAATGAATC GGTTAAATCA CCTTCGCCAA CTAAAACAAC    3360

CTTTAGAATT TCCATCTTGT GGATCTGTGT TTAAGCGCCC GCCAGGACAC TTTGCAGGTC    3420

AATTAATCAT GGAAGCAAAT CTTAAAGGGC ATCGGATTGG TGGTGTGGAA GTTTCCGAAA    3480

AACACGCTGG TTTTATGATT AATGTGGTAG ATGGCACAGC TAAAGATTAT GAAGATTTGA    3540

TTGCTTATGT CATTGAGACA GTTGAAAACC ATTCGGTGT CAGGCTTGAA CCAGAAGTTC    3600

GGATTATTGG GGAAAACCTG TAACCATTTA TTGATAATTA AGAAAGTAC CGTGGAGGAT    3660

TTATGACAAT TGACTAAGCC AATTATCACA TTTAACAATG TTTAAAAAAC ATTTGAGGAC    3720

AGTGGAACAC AGGTTCTAAA GAACATTAAC TTTGACCTTG AAGAAGGAAA ATTTTACACC    3780

CTGCTTGGAG CTTCTGGCTC TGGAAAATCA ACTATTTTAA ATATTATGGC GGGCCTACTA    3840

GATGCCAGCA GCGGAGACAT TTATTTAGAT GGGGAACGTA TTAATGATTT GCCGATTAAT    3900
```

```
AAACGTGACA TTCATACCGT TTTCCAAAAT TATGCCCTCT TCCCTCATAT GACTGTTTTT    3960

GAGAATGTTG CCTTTGCTTT GAAGCTGAAG AAAGTGGACA AGAAAGAGAT TGCTAAGCGC    4020

GTGAAAGAAA CCTTGAAAAT GGTTCAATTA GAAGGGTATG AAAATCGTTC TATCCAGAAG    4080

TTATCTGGTG GTCAACGTCA ACGTGTTGCC ATTGCGCGTG CGATTATCAA TCAACCGCGT    4140

GTGGTCTTAC TTGACGAACC ACTCTCAGCC CTTGATTTGA AATTAAGAAC AGAGATGCAA    4200

TATGAATTAC GTGAATTGCA ACAACGTCTA GGCATTACCT TTGTTTTTGT TACTCACGAT    4260

CAAGAAGAAG CCTTGGCCAT GAGTGATTGG GTTTTTGTCA TGAATGAAGG TGAAATTGTT    4320

CAGTCGGGAA CACCAGTGGA TATTTATGAT GAGCCAATTA ATCATTTGT TGCTAATTTT    4380

ATTGGAGAAT CTAATATTAT TAACGGTACC ATGATTGAAG ACTATCTTGT CTCCTTTAAC    4440

GGGAAAGAAT TTGAATCTGT GGACGGTGGG ATGCGCCCTA ATGAGCCTGT TGAAGTGGTT    4500

ATTCGTCCTG AAGATCTTCA AATTACTTTG CCAGAAGAAG GGAAATTACA AGTTAAGGTT    4560

GATACCCAAT TATTCCGCGG GGTTCACTAC GAAATTATTG CCTATGATGA ATTGGGTAAT    4620

GAATGGATGA TTCATTCTAC CCGCAAAGCT ATCGAGGGAG AAGTTATCGG ATTAGACTTT    4680

ACCCCTGAAG ATCTTCATAT CATGCGTCTT AATGAGACTG AAGAGGAATT TGATGCCCGT    4740

ATTGAAGAAT ATGTGGAAAT GGATGAGCCT GAAGATGGAT TGATTAATGC CATTGAGGAG    4800

GAGCGTAATG AAGAAAACCT CTAGTCTTTT TTCGATTCCT TACTTCTTAT GGATTCTCTT    4860

CTTTGTTGTG GCACCAGTCA CTCTCTTGTT TTACAAGTCC TTTTTTGACA TAGAAGGGCG    4920

CGTGACCTTA GCCAATTATG AAACCTTTTT TAGCTCTTGG ACCTATTTGA GAATGAGTGT    4980

GAATTCTATT TTATACGCTG GTATTATCAC ACTCGTCACG CTCTTGATTT CATATCCTAC    5040

GGCTCTCTTT TTAACGCGCC TAAAGCACAA GCAGTTGTGG CTTATGCTCA TTATTTTGCC    5100

AACTTGGGTA AACTTATTGC TAAAAGCCTA TGCCTTTATG GGAATCTTTG GTCAACAAGG    5160

AGGAATTAAC AGCTTTTTAA CCTTTATGGG GATTGGCCCG CAGCAAATCC TTTTCACGGA    5220

TTTCTCCTTC ATTTTTGTAG CCTCTTACAT TGAGCTCCCT TTTATGATGT TACCGATTTT    5280

TAACGCTTTG GATGATATTG ACCATAATGT CATTAATGCC AGTCGCGACC TAGGAGCTAG    5340

TGAATTTCAG GCCTTCTCAA AAGTTATTTT TCCCCTTTCT TTAAATGGGG TTAGGGCAGG    5400

TGTTCAGTCT GTCTTTATCC CAAGTTTGAG TCTCTTTATG TTAACCCGTT TGATTGGTGG    5460

AAACCGCGTG ATTACACTTG GTACAGCCAT TGAACAACAT TTTTTGACCA CCCAAAACTG    5520

GGGAATGGGA TCAACCATAG GTGTGGTGTT AATCTTAACC ATGGTTGCTA TTATGTGGCT    5580

CACAAAGGAG AAAAGTAAAT GAAAAAATTT GCCAATCTTT ATTTAGCGAG TGTCTTTGTT    5640

TTACTCTACA TTCCTATTTT TTATTTGATT TTCTATTCTT TCAACAAAGG TGGGGATATG    5700

AATGGTTTTA CAGGATTTAC CCTTGAGCAT TACCAAACCA TGTTTGAGGA TAGTCGTCTC    5760

ATGACAATCT TACTGCAAAC CTTTGTTCTT GCTTTTAGTA GCGCTCTACT AGCAACGATT    5820

ATTGGGACCT TTGGAGCTAT CTTTATCCAC CATGTTAGAG GTAAGTACCA AAATGCCATG    5880

CTATCAGCCA ATAATGTCTT GATGGTATCA CCAGATGTCA TGATTGGGGC TTCCTTTTTA    5940

ATTTTTTTA CATCATTGAA GTTCAGCTG GGCATGTCTT CAGTTTATT AAGTCATATT    6000

GCTTTTTCGA TTCCTATTGT GGTTTTGATG GTATTGCCGC GCTTGAAAGA GATGAATCAA    6060

GACATGGTCA ACGCCGCTTA TGATTTGGGA GCTAATTATT TCCAAATGCT CAAAGAAGTC    6120

ATGCTGCCAT ACTTAACACC AGGGATTATT GCAGGTTATT TATGGCCTT TACCTATTCC    6180

TTAGATGATT TTGCAGTGAC TTTCTTTTTG ACTGGAAATG GTTTTACTAC TTTATCTGTT    6240

GAGATTTATT CGCGGGCTCG TCAGGGAATT TCCTTGGATA TCAATGCTTT GTCAACCATC    6300
```

```
GTTTTCTTTT TCTCCATCCT CTTAGTGATC GGTTATTATT ATATGTCACA GGACAAGGAG    6360

GAAAAACATG CGTAAACTTT ATTCCTTTCT AGCAGGAGTT TTGGGTGTTA TTGTTATTTT    6420

AACAAGCCTT TCTTTCATCT TGCAGAAAAA ATCGGGTTCT GGTAGTCAAT CGGATAAATT    6480

AGTTATTTAT AACTGGGGAG ATTACATTGA TCCAGCTTTG CTCAAAAAAT TCACCAAAGA    6540

AACGGGCATT GAAGTGCAGT ATGAAACTTT CGATTCTAAT GAAGCCATGT ACACTAAAAT    6600

CAAGCAGGGC GGAACCACTT ACGACATTGC TGTTCCTAGT GATTACACCA TTGATAAAAT    6660

GATCAAAGAA AACCTACTCA ATAAGCTT                                       6688
```

(2) INFORMATION FOR SEQ ID NO:6:

(i) SEQUENCE CHARACTERISTICS:
        (A) LENGTH: 4973 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes
        (B) STRAIN: Clinical Isolate SP-55-3

(ix) FEATURE:
        (A) NAME/KEY: misc_feature
        (B) LOCATION:1934
        (D) OTHER INFORMATION: /note= "N = adenine or cytosine or
            guanine or thymine"

(ix) FEATURE:
        (A) NAME/KEY: misc_feature
        (B) LOCATION: 3740
        (D) OTHER INFORMATION: /note= "N = adenine or cytosine or
            guanine or thymine"

(xi) SEQUENCE DESCRIPTION: SEQ ID NO:6:

```
AAGCTTGTTC AGGTAGGCAC GCAAACAGTC TTAGAACAGT TACCAATGGC GTTAATTGAC      60

AAGGGAGTTG TTTTCAGTGA TTTTTATACG GCGCTTGAGG AAATCCCAGA AGTAATTGAA     120

GCTCATTTTG GTCAGGCATT AGCTTTTGAT GAAGACAAAC TAGCTGCCTA CCACACTGCT     180

TATTTTAATA GCGCAGCCGT GCTCTACGTT CCTGATCACT TGGAAATCAC AACTCCTATT     240

GAAGCTATTT TCTTACAAGA TAGTGACAGT GACGTTCCTT TTAACAAGCA TGTTCTAGTG     300

ATTGCAGGAA AAGAAAGTAA GTTCACCTAT TTAGAGCGTT TGAATCTAT TGGCAATGCC      360

ACTCAAAAGA CCAGCGCTAA TATCAGTGTA GAAGTGATTG CCCAAGCAGG CAGCCAGATT     420

AAATTCTCGG CTATCGACCG CTTAGGTCCT TCAGTGACAA CCTATATTAG CCGTCGAGGA     480

CGTTTAGAGA AGGATGCCAA CATTGATTGG GCCTTAGCTG TGATGAATGA AGGCAATGTC     540

ATTGCTGATT TGACAGTGA TTTGATTGGT CAGGGCTCAC AAGCTGATTT GAAAGTTGTT      600

GCAGCCTCAA GTGGTCGTCA GGTACAAGGT ATTGACACGC GCGTGACCAA CTATGGTCAA     660

CGTACGGTCG GTCATATTTT ACAGCATGGT GTGATTTTGG AACGTGGCAC CTTAACGTTT     720

AACGGGATTG GTCATATTCT AAAAGGCGCT AAGGGAGCTG ATGCTCAACA AGAAAGCCGT     780

GTTTTGATGC TTTCTGACCA AGCAAGAGCC GATGCCAATC CAATCCTCTT AATTGATGAA     840

AATGAAGTAA CAGCAGGTCA TGCAGCTTCT ATCGGTCAGG TTGACCCTGA AGATATGTAT     900

TACTTGATGA GTCGAGGACT GGATCAAGAA ACAGCAGAAC GATTGGTTAT TAGAGGATTC     960

CTAGGAGCAG TTATCGCTGA AATTCCTATT CCATCAGTCC ACCAAGAGAT TATTAAGGTT    1020

TTAGATGAGA AATTGCTTAA TCGTTAAGAC CTACTGCCAA AAAGAAAGAG GTTAGTATTG    1080
```

```
CTAGACGCAA AAGACATCAA ACAAGACTTT CAAATCTTAA ATCAACAAGT CAATGATGAA    1140

CCCCTTGTTT ATTTGGATAA TGCCGCCACC ACACAAAAAC CGGCGCTTGT TCTTGAGGCT    1200

TTGCAATCCT ATTATCAAGA AGATAATGCT AATGTCCACC GAGGAGTTCA TACCTTGGCT    1260

GAACGTGCAA CGCACAAATA TGAGGCCAGT CGCCAGCAGG TTGCTGACTT TATTCATGCT    1320

AAATCAAGTA AGGAAGTGCT CTTTACCAGA GGAACAACAA CCAGTTTGAA TTGGGTTGCT    1380

CGGTTTGCAG AGCAGGTCTT GACGCCAGAA GATGAGGTGT TGATTTCGAT TATGGAGCAT    1440

CATGCCAATA TCATTCCTTT GGCAACAAGC CTGTCAAAAA ACAGGAGCAA GGTTAGTCTA    1500

TGTTTATTTA AAAGATGGCC AACTTGACAT GGACGATTTG GCAAACAAAT TGACGACAAA    1560

AACACGTTTT GTTAGCCTAG TACATGTCTC CAATGTTCTT GGTTGCATCA ATCCCATTAA    1620

AGAAATTGCC AAGCTGGCAC ATGCTAAAGG AGCCTACCTT GTTGTTGACG GTGCCCAGTC    1680

GGTTCCACAT TTGGCTATTG ATGTTCAAGA CTTGGATTGT GATTTCTTTG CTTTTTCAGC    1740

TCATAAGATG TTGGGGCCAA CAGGTTTGGG TGTTCTTTAC GGCAAAGAAG AGCTTTTGAA    1800

TCAAGTGGAG CCTCTTGAAT TTGGCGGAGA ATGATTGAT TTTGTTTACG AACAAGAGGC    1860

CACTTGGAAA GAATTGCCCT GGAAGTTTGA AGCAGGAACA CCTCACATAG CTGGTGCTAT    1920

TGGGCTAAGC GCANCCATTT CTTACCTTCA GAGACTAGGC ATGGCTGATA TACATGCGCA    1980

TGAAGCAGAA CTAATAGCCT ATGTCTTGCC GAAATTAGAA GCTATTGAGG GGCTTACCAT    2040

ATATGGACCA AGCCAGCCTA GTGCAAGATC TGGTCTGATT TCTTTTAATC TGGATGATTT    2100

GCATCCTCAT GACTTGGCAA CAGCCTTGGA CTATGAAGGT GTTGCAGTAA GAGCAGGGCA    2160

CCACTGCGCC CAACCTCTTC TTAGTTATTT AGGTGTACCA GCAACTGTTA GAGCAAGTTT    2220

TTATATCTAT AACACCAAGG CAGATTGTGA CCGTCTAGTC GAAGCAATTC TAAAAGCAAA    2280

GGAGTTTTTC AATGGCACTC TCTAAACTGA ACCATCTATA CATGGCTGTG GTAGCGGACC    2340

ATTCGAAACG TCCACATCAT CATGGGCAAC TAGATGGCGT AGAGGCTGTT CAACTGAATA    2400

ATCCGACTTG TGGTGATGTG ATTTCTTTGA CCGTTAAGTT TGACGAAGAT AAAATTGAAG    2460

ATATTGCTTT TGCAGGCAAC GGCTGTACCA TTTCCACAGC TTCATCAAGC ATGATGACAG    2520

ATGCTGTTAT TGGTAAAAGT AAAGAAGAAG CACTCGCGTT AGCTGATATT TTTTCAGAGA    2580

TGGTACAAGG ACAGGAAAAT CCTGCTCAAA AAGAGCTAGG TGAAGCAGAA TTGTTGGCAG    2640

GAGTTGCAAA ATTTCCACAG CGTATCAAAT GCTCTACCCT AGCTTGGAAT GCTCTCAAGG    2700

AAGCCATTAA ACGAAGTGCC AATGCTCAGC ACCTCACGGA CCAAAATGTA AAGGAAGGGA    2760

AAAATGTCTG ATATAAATGA GAAAGTAGAG CCAAAGCCAA TTGACTTAGG GGACTACCAA    2820

TTTGGATTTC ACGATGATGT AGAGCCCATT TATTCTACAG GAAAAGGATT GAGTGAGGCA    2880

GTGGTTCGCG AACTATCAGC TGCCAAAAAT GAACCTGAGT GGATGTTGGA GTTTCGTTTA    2940

AAATCCTTGG AAACCTTTAA TAAAATGCCG ATGCAAACCT GGGGAGCAGA CTTATCAGAT    3000

ATTAACTTTG ATGATATCAT TTACTATCAA AAAGCATCTG ATAAGCCAGC TCGTTCTTGG    3060

GATGATGTTC CAGAAAAAAT AAAAGAAACC TTTGATCGTA TTGGAATTCC AGAAGCAGAA    3120

CGTGCTTATC TTGCTGGGGC ATCAGCTCAG TATGAGTCAG AAGTGGTTTA CCATAACATG    3180

AAGGGTGAAT TTGAAAAGCT AGGGATTATC TTTACAGATA CCGATTCCGC CCTCAAAGAA    3240

TATCCTGATT TGTTCAAACA ATACTTTGCC AAACTGGTTC CGCCAACAGA CAACAAATTA    3300

GCAGCCCTCA AATTCAGCAG TTTGGTCTGG TGGTACCTTT ATTTATGTTC CTAAAGGGGT    3360

CAAGGTAGAT ATCCCTTTGC AAACTTATTT CCGCATTAAC AATGAAAATA CTGGTCAATT    3420
```

-continued

```
TGAGCGGACA TTGATTATTG TTGATGAAGG AGCAAGTGTT CATTATGTTG AAGGATGTAC    3480

AGCTCCCACT TATTCAAGTA ACAGCTTACA TGCTGCTATC GTTGAAATCT TTGCGCTTGA    3540

CGGTGCATAC ATGCGTTATA CCACCATTCA AAACTGGTCA GACAATGTGT ATAATCTAGT    3600

AACAAAACGT GCACGCGCCC TTACGGATGC AACAGTGGAA TGGATTGATG CAATCTAGG     3660

AGCTAAAACC ACCATGAAGT ACCCTTCTGT TTACCTTGAT GGGCCAGGTG CGCGTGGCAC    3720

CATGCTGTCT ATTGCCTTTN TAACGCAGGC CAACACCAAG ATACAGGGGC TAAAATGATT    3780

CACAATGCTC CCCATACATC ATCATCAATT GTGTCAAAAT CAATTGCCAA GTCTGGTGGT    3840

AAAGTAGATT ATCGTGGCCA AGTGACCTTT AACAAGCAAT CTAAAAAATC CGTTTCCCAT    3900

ATTGAATGTG ATACTATTTT GATGGACGAT ATTTCTAAAT CAGATACGAT CCCATTTAAC    3960

GAAATTCATA ATTCACAGGT GGCGTTAGAA CATGAAGCTA AAGTGTCTAA GATTTCTGAA    4020

GAACAACTCT ACTATCTCAT GAGCCGTGGC TTATCAGAAA GCGAAGCCAC AGAGATGATT    4080

GTCATGGGAT TTGTGGAGCC TTTTACCAAA GAATTGCCAA TGGAATATGC GGTCGAACTC    4140

AATCGATTGA TTTCCTATGA GATGGAAGGT TCTGTCGGTT AATTGCATTT TCTCTTATCC    4200

ATCTGAAAGA TCTTTGAGAT AGGATTTTAT GAGTTGTAGT ACTAACCCCA AGTGGTTAGT    4260

TTTTAGTTGC CTTGAACACG TAAGATAACA TATCAAAAAC CTCTGTGCTT TGACAGAGGT    4320

TTTTGATAAT TCATTATTGG CGTCCCATTG CAAAGACAAC GAGGCTTAGT AAAAGGATAG    4380

TAATTATAAA GATAGCTAAG CAAATAAGCA AGAAAGTGTG GTTGTGATTC ATAAAATCTT    4440

CGACTCTTTC CAAGTACGAT TGCTTTTTAG TGGCTTTGAA GTGCTGCTGT TTAGGTGATG    4500

TTTCTTTTTT GGTTTGTGGC ACTAATTTTT CGAGTTTTTG GCGTGCTTTT TGGATAAGGT    4560

CTTACTATCT TTAAACCCTT TCTCAGTCAA GGCATTAACG AAAGGATGTC TATAAAACTC    4620

TCCGTTTTGA TCTGACCAAT CTCCGACCCC CATGACAATA GTAATGAGTC GAGTTTTGCC    4680

TCTTTTGGCA GTTATCATGG CGTTAAAAGC AGCACTGGGA CTAGAACCTG TTTTTAATCC    4740

ATCAACTCCT TTCATACCAA ATTGATTGTC TGGGAGAGAG TGGTTATAGG TGTGAAATTC    4800

TTCTTCATAT GGCGTTCCTA CCATAGTGTG CACAACAGAT TTATTTGTAA AGGAGATAAT    4860

TTCAGGGTAT TTTTTTAAGA AGGCATAGAG TAACTTGGAC AAATCTCGAG CGGTCGTAAT    4920

ATTTGAAGCA GATAAATCAT ATTTAGTAGG ATTATAATAA CCTTGAAAAG CTT           4973
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:7:

```
CGACGTTGTA AAACGACGGC CAGT                                             24
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:8:

CAGGAAACAG CTATGAC                                                                                         17